(12) United States Patent
Park et al.

(10) Patent No.: US 12,159,227 B2
(45) Date of Patent: Dec. 3, 2024

(54) SYSTEM FOR PREDICTING OPTICAL PROPERTIES OF MOLECULES BASED ON MACHINE LEARNING AND METHOD THEREOF

(71) Applicant: Korea University Research and Business Foundation, Seoul (KR)

(72) Inventors: Sungnam Park, Seoul (KR); Joon Young Joung, Seoul (KR); Min Hi Han, Seoul (KR); Dong Hun Choi, Seoul (KR); Min Seok Jeong, Hanam-si (KR)

(73) Assignee: Korea University Research and Business Foundation, Seoul (KR)

( * ) Notice: Subject to any disclaimer, the term of this patent is extended or adjusted under 35 U.S.C. 154(b) by 543 days.

(21) Appl. No.: 17/199,618

(22) Filed: Mar. 12, 2021

(65) Prior Publication Data
US 2021/0287137 A1 Sep. 16, 2021

(30) Foreign Application Priority Data

Mar. 13, 2020 (KR) ......................... 10-2020-0031586
Mar. 31, 2020 (KR) ......................... 10-2020-0039313

(51) Int. Cl.
*G06N 3/08* (2023.01)
*G06N 3/00* (2023.01)
(Continued)

(52) U.S. Cl.
CPC ............... *G06N 3/08* (2013.01); *G06N 3/002* (2013.01); *G06N 3/04* (2013.01); *G06N 20/00* (2019.01);
(Continued)

(58) Field of Classification Search
CPC .... G06F 2218/08; G06N 20/00; G06N 3/002; G06N 3/04; G06N 3/08; G06N 7/00; G16C 20/30; G16C 20/70
See application file for complete search history.

(56) References Cited

U.S. PATENT DOCUMENTS 6,898,533 B1 * 5/2005 Miller .................... G01N 21/25
702/30
7,996,156 B2 * 8/2011 Beger .................... G01N 33/48
703/2

(Continued)

FOREIGN PATENT DOCUMENTS

JP 5211347 B2 6/2013

OTHER PUBLICATIONS

Wang et al., "Molecular Property Prediction Based on a Multichannel Substructure Graph" Jan. 30, 2020, pp. 18601-18614. (Year: 2020).*

(Continued)

*Primary Examiner* — Kevin W Figueroa
*Assistant Examiner* — Chase P. Hinckley
(74) *Attorney, Agent, or Firm* — NSIP Law

(57) ABSTRACT

Disclosed are a system for predicting optical properties of molecules based on machine learning and a method thereof. More particularly, the system for predicting optical properties according to an embodiment includes a preprocessor that receives molecular information of a target molecule and surrounding molecules, and vectorizes the molecular information of a target molecule and surrounding molecules; a feature extractor that receives the vectorized information of the target molecule and surrounding molecules and extracts the features of the target molecule and surrounding molecules; an integrated feature extractor that receives both features of the target molecule and surrounding molecules and extract the integrated features of the target molecule and (Continued)

surrounding molecules by using an algorithm; and an optical property predictor that receives the integrated features of the target molecule and surrounding molecules and predicts optical properties of the target molecule affected by surrounding molecules.

6 Claims, 30 Drawing Sheets

(51) Int. Cl.
*G06N 3/04* (2023.01)
*G06N 20/00* (2019.01)
*G16C 20/30* (2019.01)
*G16C 20/70* (2019.01)
*G06N 7/00* (2023.01)
*G16B 15/20* (2019.01)

(52) U.S. Cl.
CPC ............. *G16C 20/30* (2019.02); *G16C 20/70* (2019.02); *G06F 2218/08* (2023.01); *G06N 7/00* (2013.01); *G16B 15/20* (2019.02)

(56) References Cited

U.S. PATENT DOCUMENTS

| | | | | |
|---|---|---|---|---|
| 11,238,278 | B1* | 2/2022 | Swanson | G06V 30/413 |
| 11,526,765 | B2* | 12/2022 | Shanthamallu | G06N 3/045 |
| 11,531,710 | B2* | 12/2022 | Yin | G06F 18/2163 |
| 11,670,403 | B2* | 6/2023 | Kim | G06N 3/047 |
| | | | | 706/16 |
| 11,721,413 | B2* | 8/2023 | Tagade | G06N 3/045 |
| | | | | 703/11 |
| 11,854,671 | B2* | 12/2023 | Rong | G16C 20/30 |
| 2003/0229456 | A1* | 12/2003 | Beger | G16C 20/30 |
| | | | | 702/27 |
| 2017/0193200 | A1* | 7/2017 | Hsu | G16C 20/30 |
| 2020/0050737 | A1* | 2/2020 | Kajino | G06N 3/042 |
| 2020/0110777 | A1* | 4/2020 | Yin | G06F 16/9024 |
| 2020/0125958 | A1* | 4/2020 | Ishiguro | G06N 5/04 |
| 2020/0176087 | A1* | 6/2020 | Colby | G06N 3/047 |
| 2020/0294630 | A1* | 9/2020 | Miller | G06N 3/045 |
| 2020/0334495 | A1* | 10/2020 | Al-Rfou | G06N 3/084 |
| 2020/0349451 | A1* | 11/2020 | Suzuki | G06N 3/045 |
| 2020/0365235 | A1* | 11/2020 | Hama | G06F 16/9024 |
| 2020/0372334 | A1* | 11/2020 | Carolan | G02F 1/35 |
| 2021/0081505 | A1* | 3/2021 | Bai | G06N 3/04 |
| 2021/0158904 | A1* | 5/2021 | Rong | G16C 20/70 |
| 2021/0209759 | A1* | 7/2021 | Smith | G06N 3/045 |
| 2021/0217501 | A1* | 7/2021 | Matsushita | G06N 20/00 |
| 2021/0241176 | A1* | 8/2021 | Yoo | G16C 20/30 |
| 2021/0264110 | A1* | 8/2021 | McCarthy | G16C 20/50 |
| 2022/0020115 | A1* | 1/2022 | Zhang | G06N 3/045 |
| 2022/0044767 | A1* | 2/2022 | Rong | G16C 20/30 |
| 2022/0101276 | A1* | 3/2022 | Banatao | G16C 20/30 |
| 2022/0165367 | A1* | 5/2022 | Priyakumar | G16B 40/30 |
| 2022/0207370 | A1* | 6/2022 | Motoki | G06N 3/045 |
| 2022/0215260 | A1* | 7/2022 | Dasoulas | G06N 3/048 |
| 2022/0223234 | A1* | 7/2022 | Asahara | G16C 60/00 |
| 2022/0230713 | A1* | 7/2022 | Maragakis | G06N 3/045 |
| 2022/0277815 | A1* | 9/2022 | Hosoumi | G06F 30/10 |
| 2022/0285038 | A1* | 9/2022 | Liu | G06N 3/08 |
| 2022/0309815 | A1* | 9/2022 | Hamaguchi | G06V 30/18057 |
| 2022/0348903 | A1* | 11/2022 | Ranganathan | C12N 15/1058 |
| 2022/0383989 | A1* | 12/2022 | Jonas | G06N 20/20 |
| 2022/0383993 | A1* | 12/2022 | Yoo | G16C 20/60 |
| 2022/0383994 | A1* | 12/2022 | Rabideau | G16C 20/70 |
| 2022/0406412 | A1* | 12/2022 | Segler | G16C 20/70 |
| 2023/0052677 | A1* | 2/2023 | Eser | G16B 15/30 |
| 2023/0075100 | A1* | 3/2023 | Zavoronkovs | G06N 3/006 |
| 2023/0159475 | A1* | 5/2023 | Chopra | C07D 413/06 |
| | | | | 514/365 |

OTHER PUBLICATIONS

Zhang et al., "SPVec: A Word2vec-Inspired Feature Representation Method for Drug-Target Interaction Prediction" Jan. 10, 2020, pp. 1-11. (Year: 2020).*

Karpov et al., "Transformer-CNN: Fast and Reliable Tool for QSAR" Feb. 26, 2020, arXiv: 1911.06603v3, pp. 1-15. (Year: 2020).*

Krenn et al., "Self-Referencing Embedded Strings (SELFIES): A 100% robust molecular string representation" Mar. 5, 2020, arXiv: 1905.13741v2, pp. 1-9. (Year: 2020).*

Han et al., "Learning Both Weights and Connections for Efficient Neural Networks" Oct. 30, 2015, arXiv: 1506.02626v3, pp. 1-9. (Year: 2015).*

Goh et al., "SMILES2vec: An Interpretable General-Purpose Deep Neural Network for Predicting Chemical Properties" Mar. 18, 2018, arXiv: 1712.02034v2, pp. 1-8. (Year: 2018).*

Jaeger et al., "Mol2vec: Unsupervised Machine Learning Approach with Chemical Intuition" Dec. 22, 2017, pp. 27-35. (Year: 2017).*

Oldenhof et al., "ChemGrapher: Optical Graph Recognition of Chemical Compounds by Deep Learning" Feb. 23, 2020, arXiv: 2002.09914v2, pp. 1-16. (Year: 2020).*

Wang et al., "SMILES-BERT: Large Scale Unsupervised Pre-Training for Molecular Property Prediction" Sep. 2019, pp. 429-436. (Year: 2019).*

Wu et al., "MoleculeNet: A Benchmark for Molecular Machine Learning" Oct. 26, 2019, arXiv: 1703.00564v3, pp. 1-65. (Year: 2019).*

Alperstein et al., "All SMILES Variational Autoencoder" Jun. 3, 2019, arXiv: 1905.13343v2, pp. 1-23. (Year: 2019).*

Bjerrum, Esben Jannik, "SMILES Enumeration as Data Augmentation for Neural Network Modeling of Molecules" May 17, 2017, arXiv: 1703.07076v2, pp. 1-7. (Year: 2017).*

Honda et al., "SMILES Transformer: Pre-trained Molecular Fingerprint for Low Data Drug Discovery" Nov. 12, 2019, arXiv: 1911.04738v1, pp. 1-9. (Year: 2019).*

Jeon et Kim, "FP2VEC: a new molecular featurizer for learning molecular properties" May 9, 2019, pp. 4979-4985. (Year: 2019).*

Hu et al., "Heterogeneous Graph Transformer" Mar. 3, 2020, arXiv: 2003.01332v1, pp. 1-11. (Year: 2020).*

Maziarka et al., "Molecule Attention Transformer" Feb. 19, 2020, arXiv: 2002.08264v1, pp. 1-16. (Year: 2020).*

Louis et al., "Global Attention based Graph Convolutional Neural Networks for Improved Materials Property Prediction" Mar. 11, 2020, arXiv: 2003.13379v1, pp. 1-11. (Year: 2020).*

Shi et al., "GraphAF: A Flow-Based Autoregressive Model for Molecular Graph Generation" Feb. 27, 2020, arXiv: 2001.09382v2, pp. 1-18. (Year: 2020).*

Flam-Shepherd et al., "Graph Deconvolutional Generation" Feb. 14, 2020, arXiv: 2002.07087v1, pp. 1-8. (Year: 2020).*

Boukouvalas et al., "Independent Vector Analysis for Data Fusion Prior to Molecular Property Prediction with Machine Learning" Nov. 1, 2018, arXiv: 1811.00628v1, pp. 1-9. (Year: 2018).*

Jin et al., "Junction Tree Variational Autoencoder for Molecular Graph Generation" Mar. 29, 2019, arXiv: 1802.04364v4, pp. 1-17. (Year: 2019).*

Jin et al., "Hierarchical Graph-to-Graph Translation for Molecules" Oct. 18, 2019, arXiv: 1907.11223v2, pp. 1-14. (Year: 2019).*

Jin et al., "Composing Molecules with Multiple Property Constraints" Feb. 8, 2020, arXiv: 2002.03244v1, pp. 1-10. (Year: 2020).*

Jin et al., "Hierarchical Generation of Molecular Graphs using Structural Motifs" Feb. 8, 2020, arXiv: 2002.03230v1, pp. 1-10. (Year: 2020).*

Hu et al., "Strategies for Pre-training Graph Neural Networks" Feb. 18, 2020, arXiv: 1905.12265v3, pp. 1-22. (Year: 2020).*

Hu et al., "Pre-Training Graph Neural Networks for Generic Structural Feature Extraction" May 31, 2019, arXiv: 1905.13728v1, pp. 1-15. (Year: 2019).*

Coley et al., "A Graph-Convolutional Neural Network Model for the Prediction of Chemical Reactivity" 2018, pp. 1-43. (Year: 2018).*

(56) References Cited

OTHER PUBLICATIONS

Klicpera et al., "Directional Message Passing for Molecular Graphs" Mar. 6, 2020, arXiv: 2003.03123v1, pp. 1-13. (Year: 2020).*

Liu et al., "N-Gram Graphs: Simple Unsupervised Representation for Graphs, with Applications to Molecules" Nov. 11, 2019, arXiv: 1806.09206v2, pp. 1-28. (Year: 2019).*

Popova et al., "MolecularRNN: Generating realistic molecular graphs with optimized properties" May 31, 2019, arXiv: 1905.13372v1, pp. 1-10. (Year: 2019).*

Lu et al., "Deep Learning for Optoelectronic Properties of Organic Semiconductors" Mar. 11, 2020, pp. 7048-7060. (Year: 2020).*

Scalia et al., "Evaluating Scalable Uncertainty Estimation Methods for DNN-Based Molecular Property Prediction" Oct. 7, 2019, arXiv: 1910.03127v1, pp. 1-52. (Year: 2019).*

Shindo et al., "Gated Graph Recursive Neural Networks for Molecular Property Prediction" Nov. 25, 2019, arXiv: 1909.00259v2, pp. 1-10. (Year: 2019).*

Schwaller et al., "Molecular Transformer: A Model for Uncertainty-Calibrated Chemical Reaction Prediction" Aug. 30, 2019, pp. 1572-1583. (Year: 2019).*

Korean Office Action issued on Apr. 18, 2022 in corresponding Korean Patent Application No. 10-2020-0039313 (5 pages in Korean).

Coley, Connor W., et al. "Convolutional embedding of attributed molecular graphs for physical property prediction." *Journal of chemical information and modeling* vol. 57, Issue 8 (2017). pp. 1-30.

Beard, Edward J., et al. "Comparative dataset of experimental and computational attributes of UV/vis absorption spectra." *Scientific data* vol. 6, Issue 307 (2019). pp. 1-11.

Ghosh, Kunal, et al. "Deep learning spectroscopy: Neural networks for molecular excitation spectra." *Advanced science* vol. 6, Issue 6 (2019): 1801367. pp. 1-7.

Zhuo, Ya, et al. "Identifying an efficient, thermally robust inorganic phosphor host via machine learning." *Nature communications* vol. 9, Issue 4377 (2018). pp. 1-10.

Coley, Connor W., et al. "Convolutional embedding of attributed molecular graphs for physical property prediction." Journal of chemical information and modeling 57.8 (2017): 1757-1772.

Zhuo, Ya, et al. "Identifying an efficient, thermally robust inorganic phosphor host via machine learning." Nature communications 9.1 (2018): 1-10.

Ghosh, Kunal, et al. "Deep learning spectroscopy: Neural networks for molecular excitation spectra." Advanced science 6.9 (2019): 1801367.

Beard, Edward J., et al. "Comparative dataset of experimental and computational attributes of UV/vis absorption spectra." Scientific data 6.1 (2019): 1-11.

Korean Office Action issued on Oct. 14, 2021, in counterpart Korean Patent Application No. 10-2020-0039313 (6 pages in Korean).

\* cited by examiner

[FIG. 1]
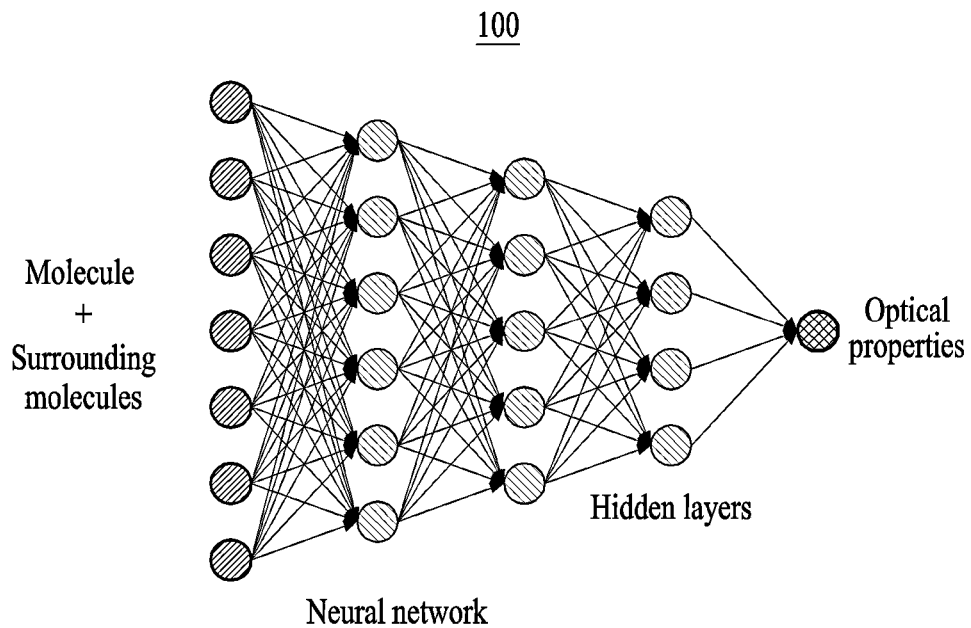
[FIG. 2]
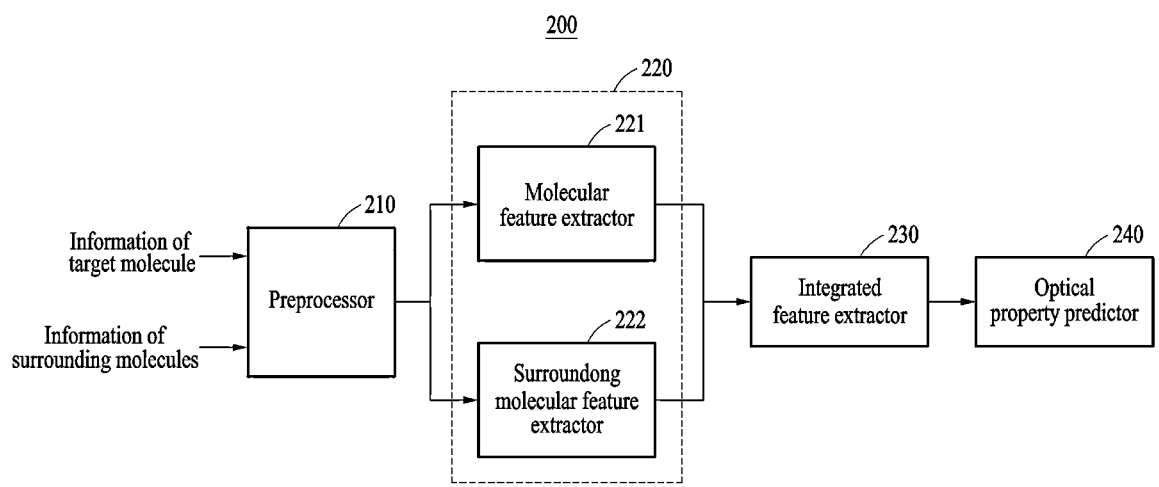

[FIG. 3]
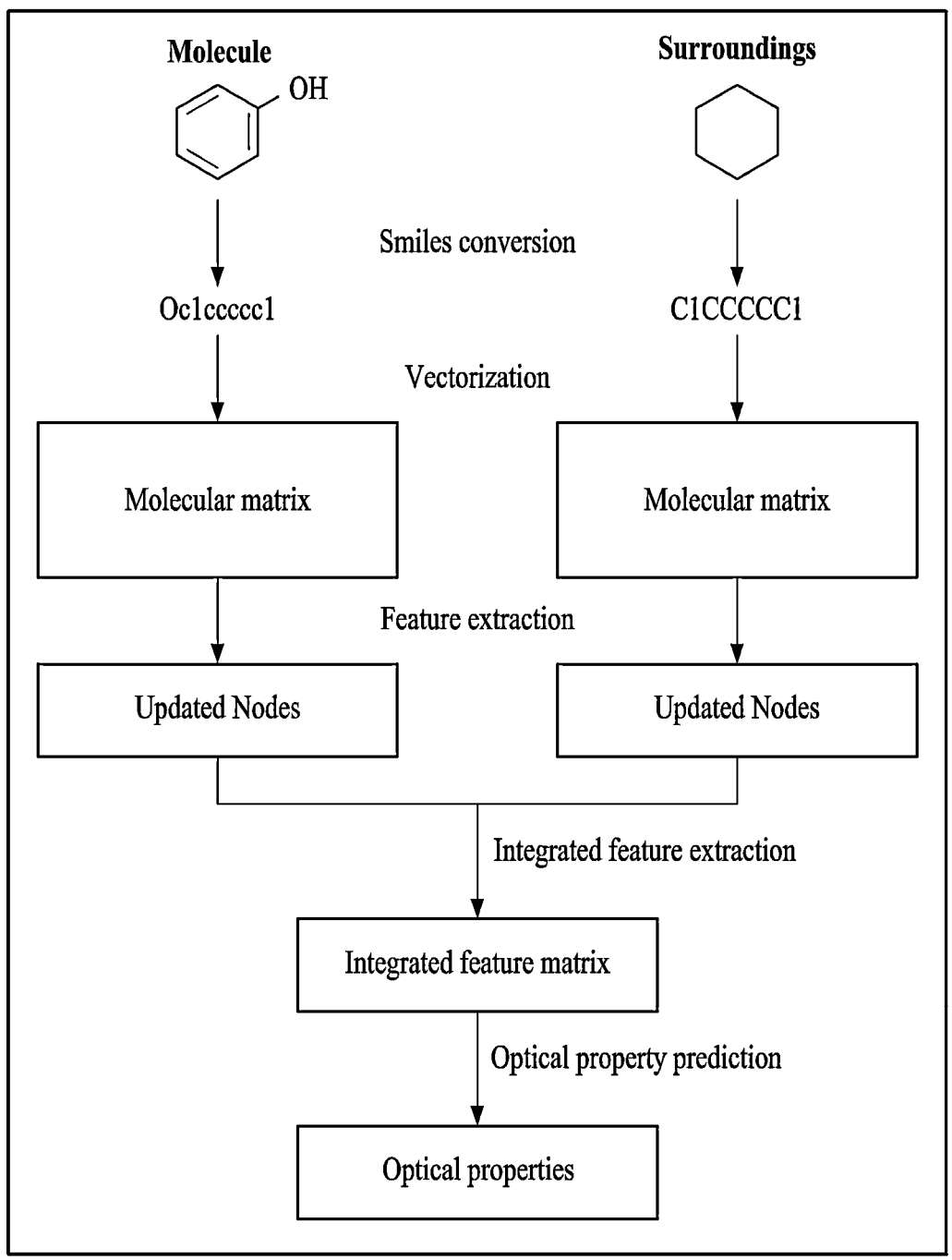

[FIG. 4]
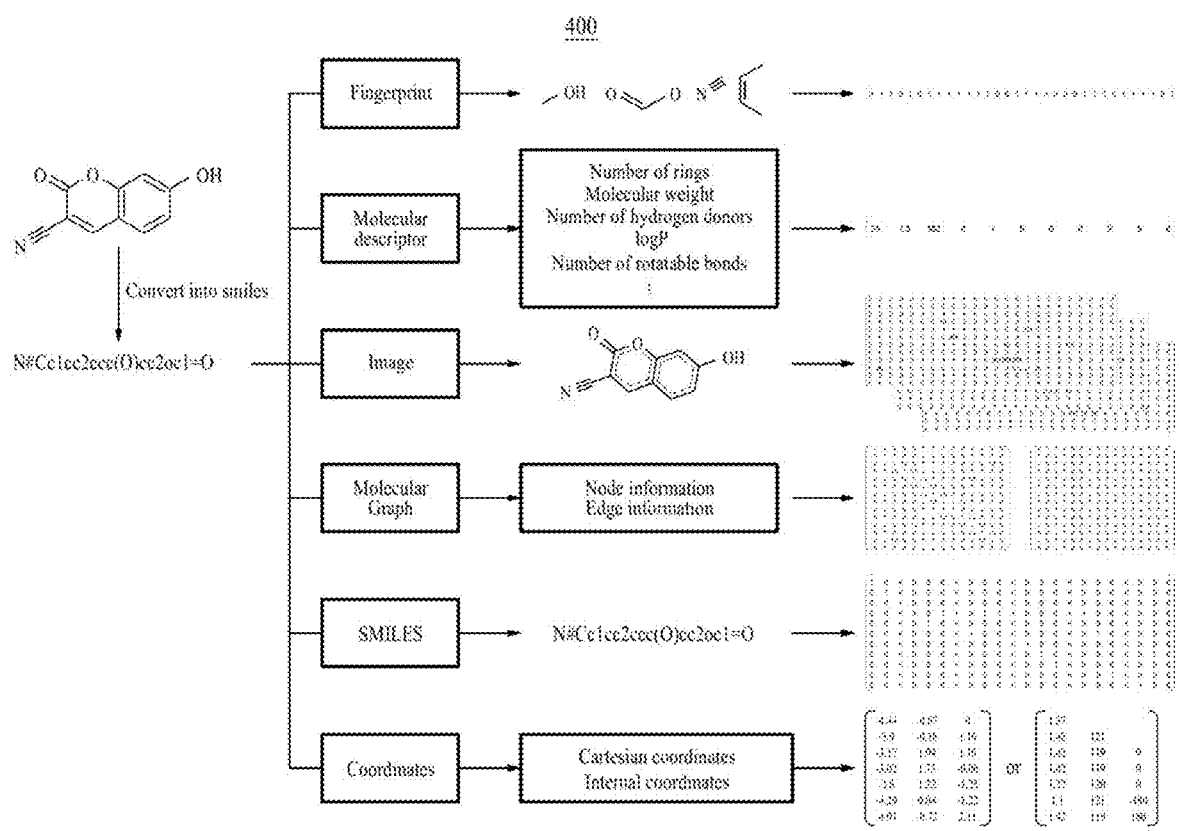

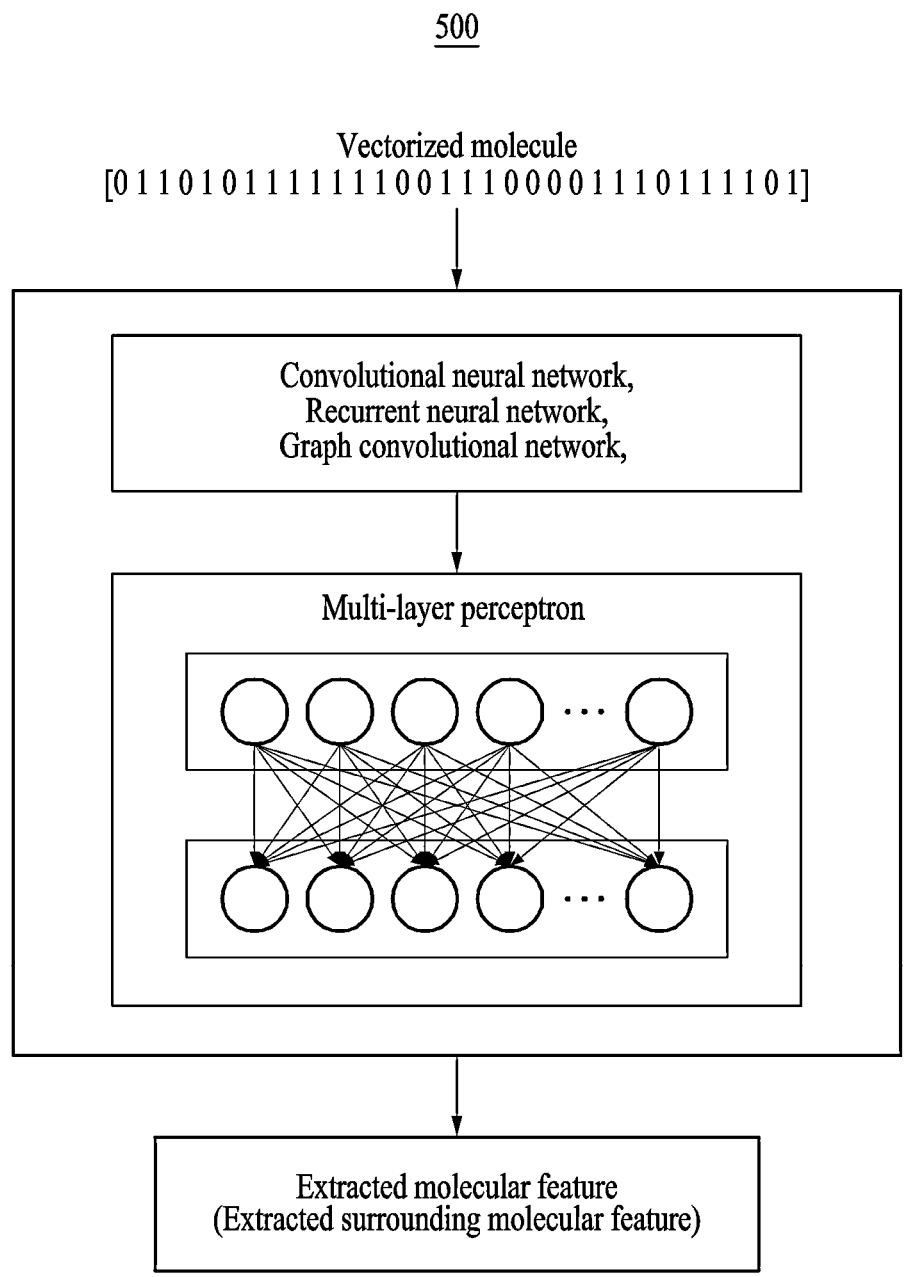

【FIG. 6】
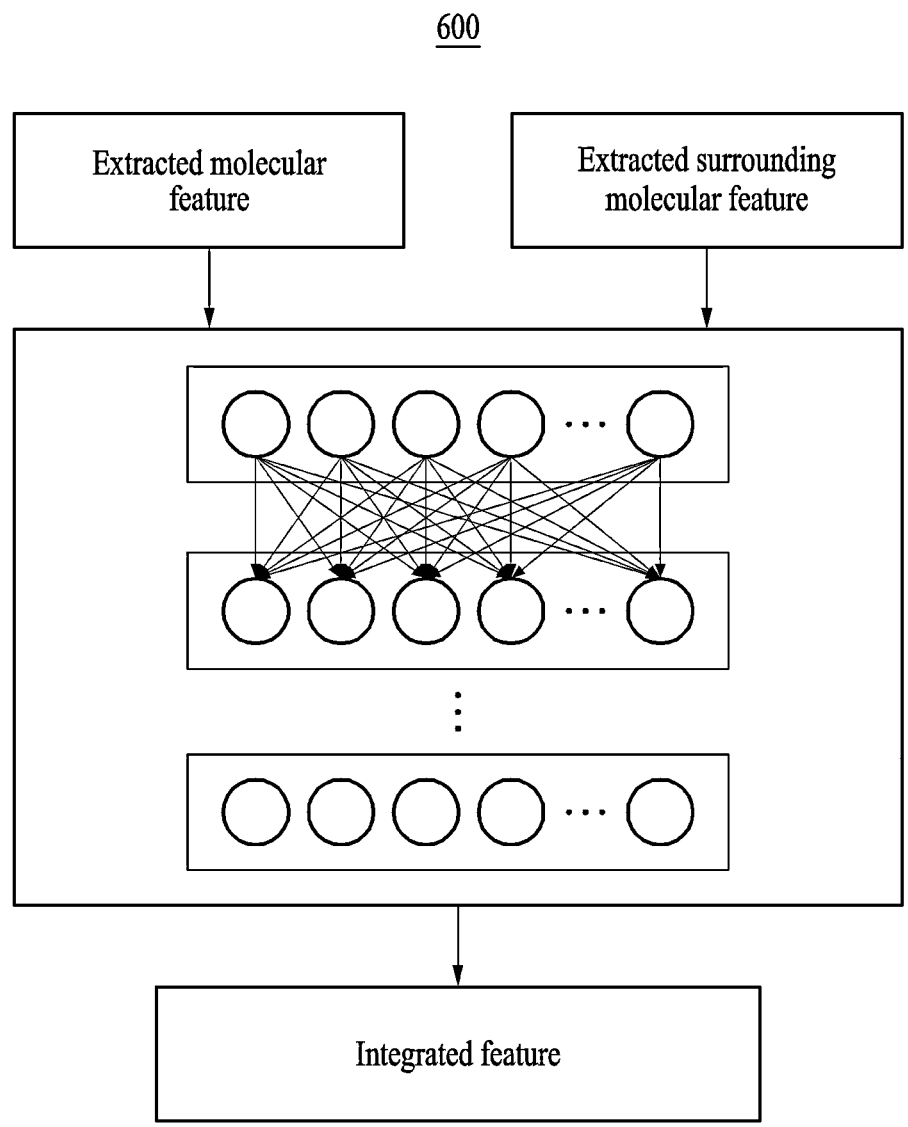

[FIG. 7]
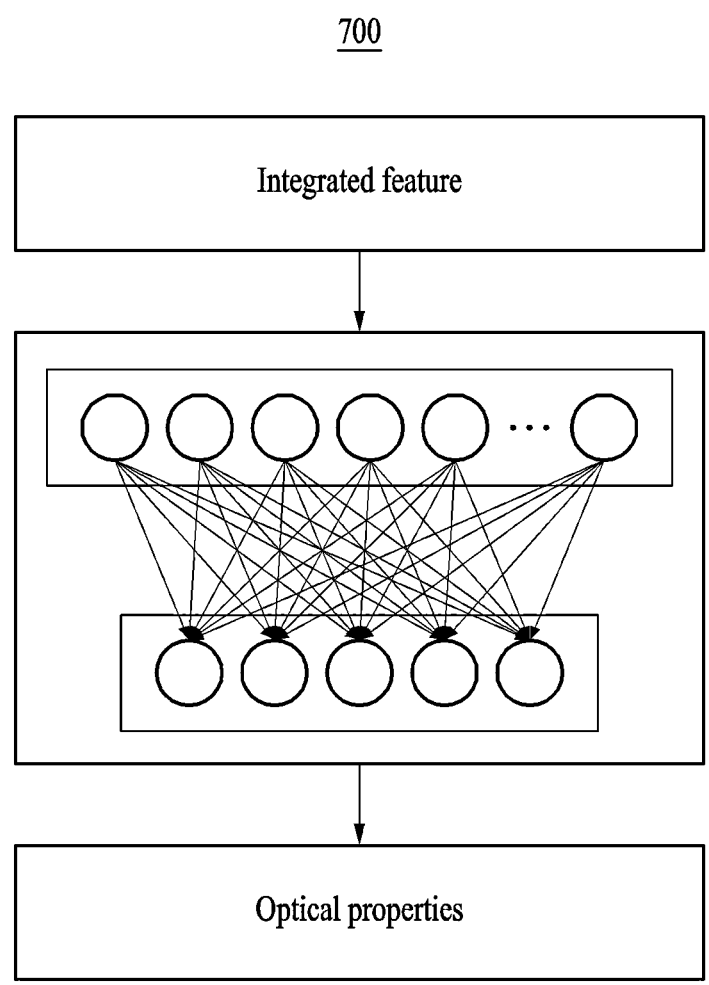

[FIG. 8]
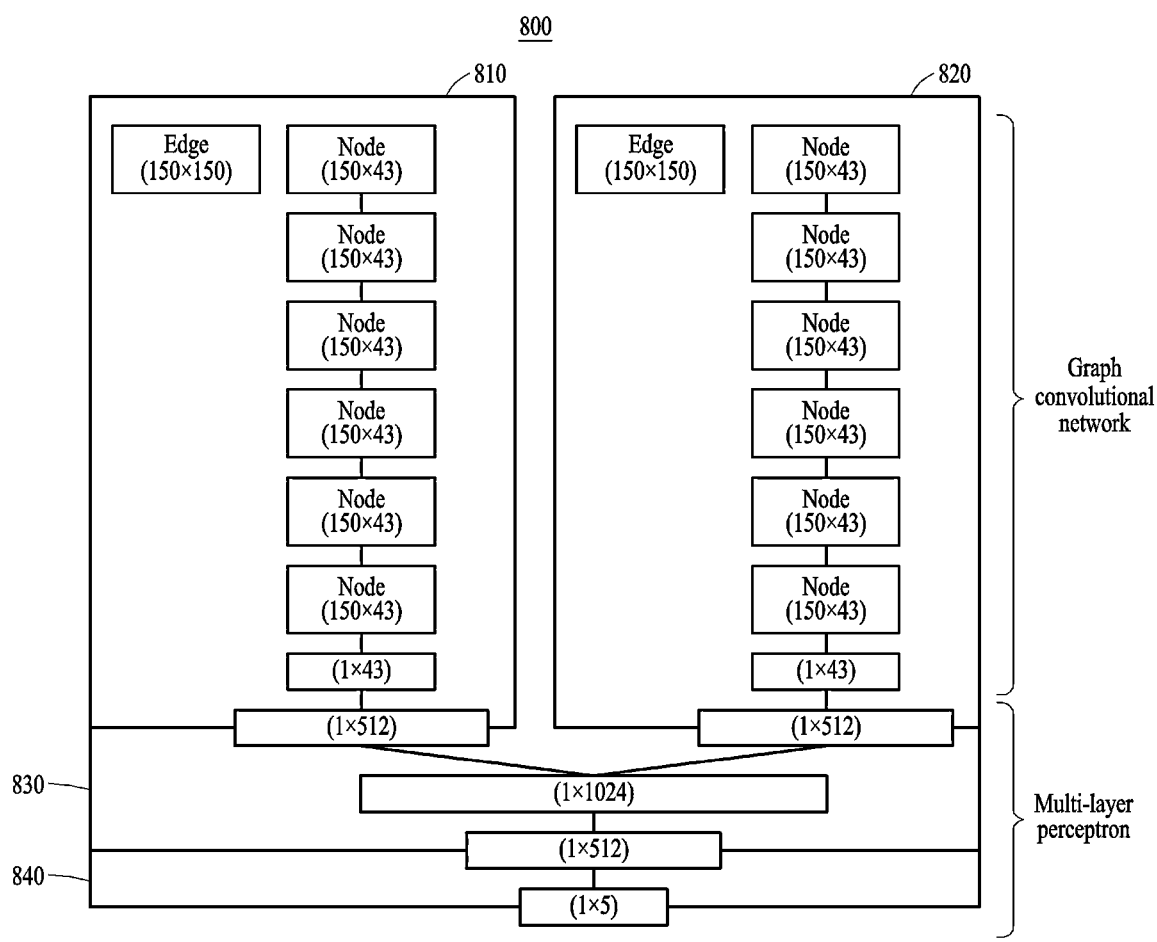

[FIG. 9A]
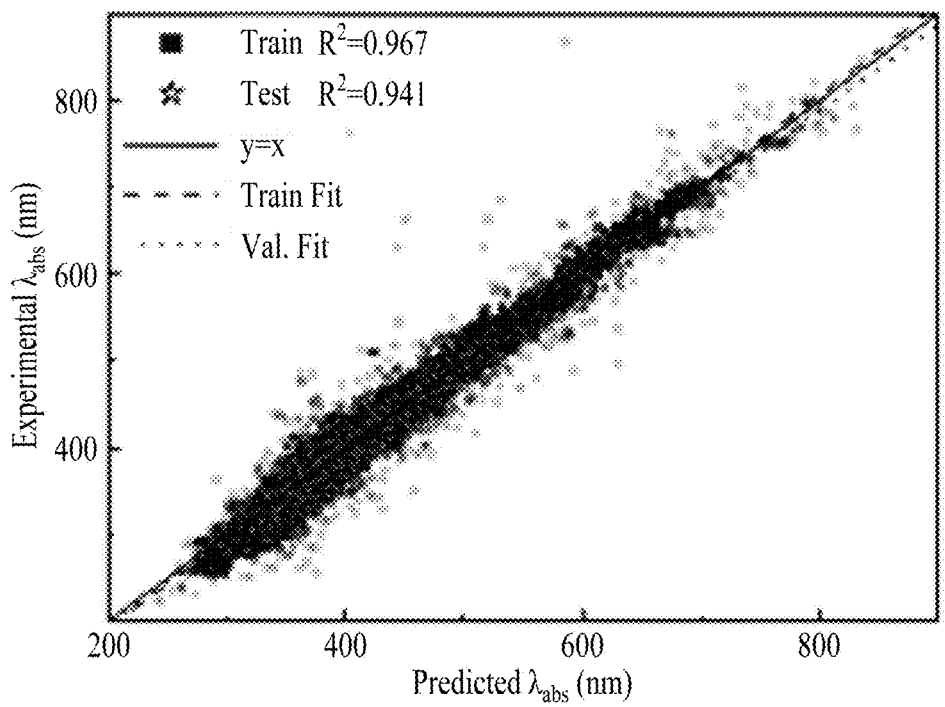

[FIG. 9B]
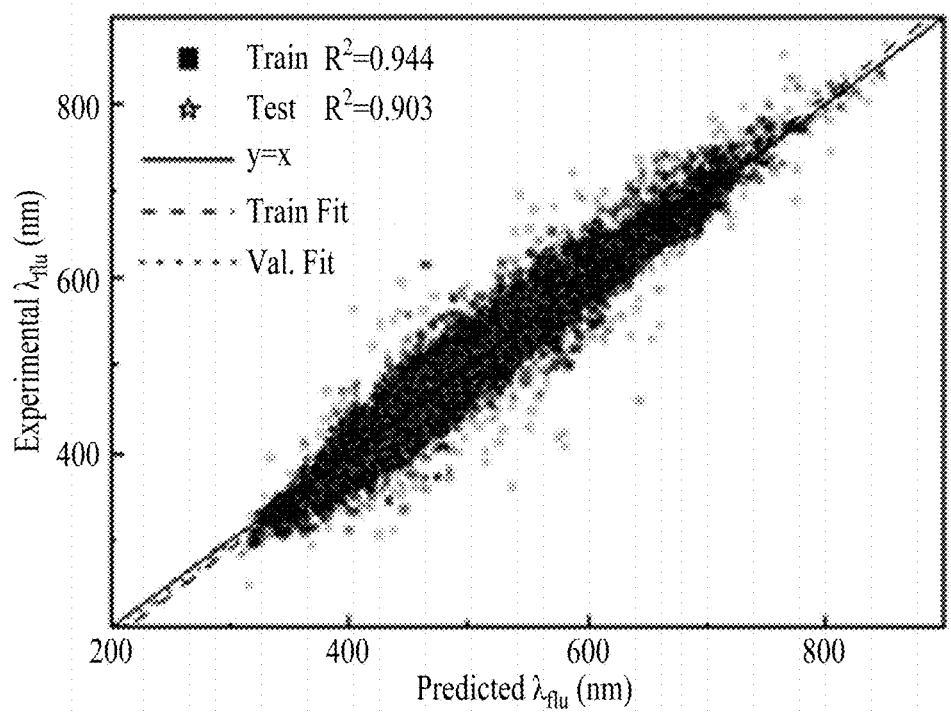

[FIG. 9C]
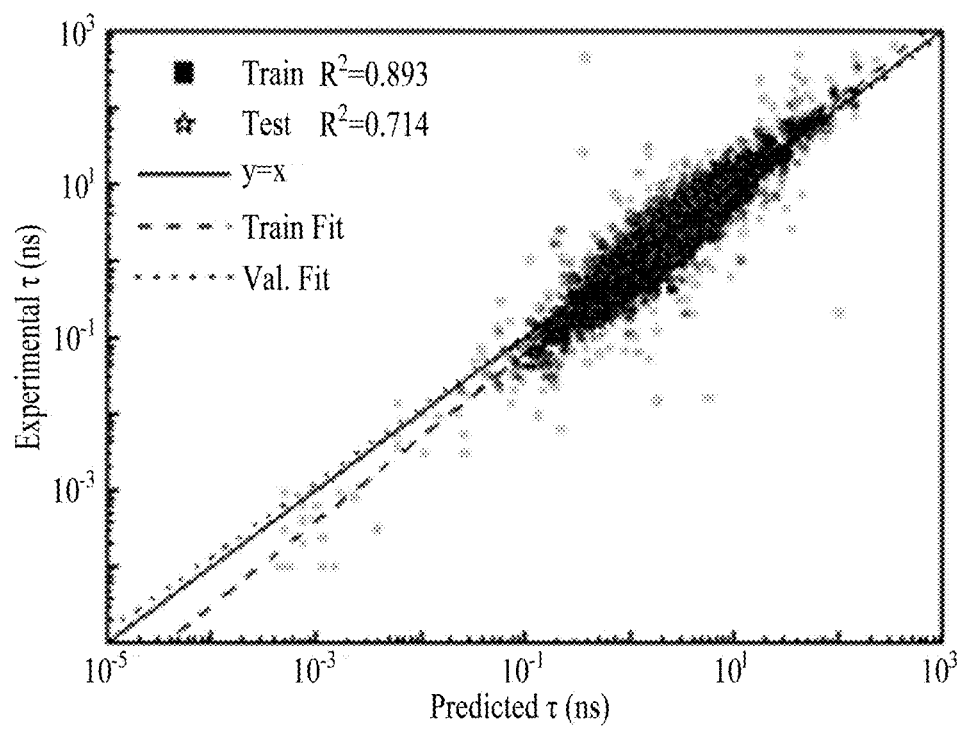

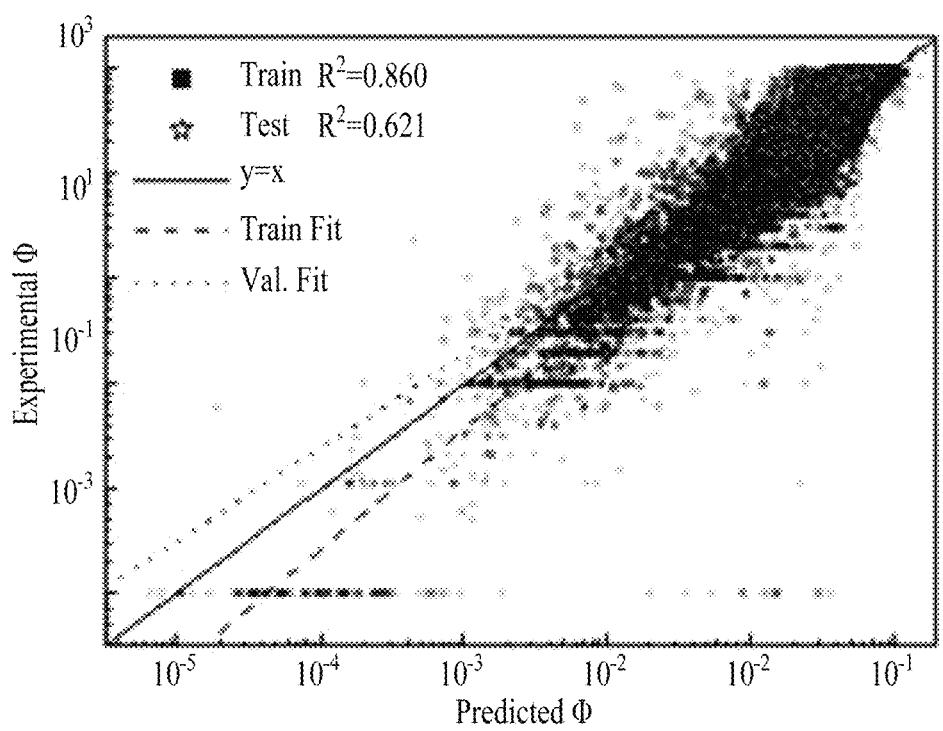
[FIG. 9D]

[FIG. 9E]
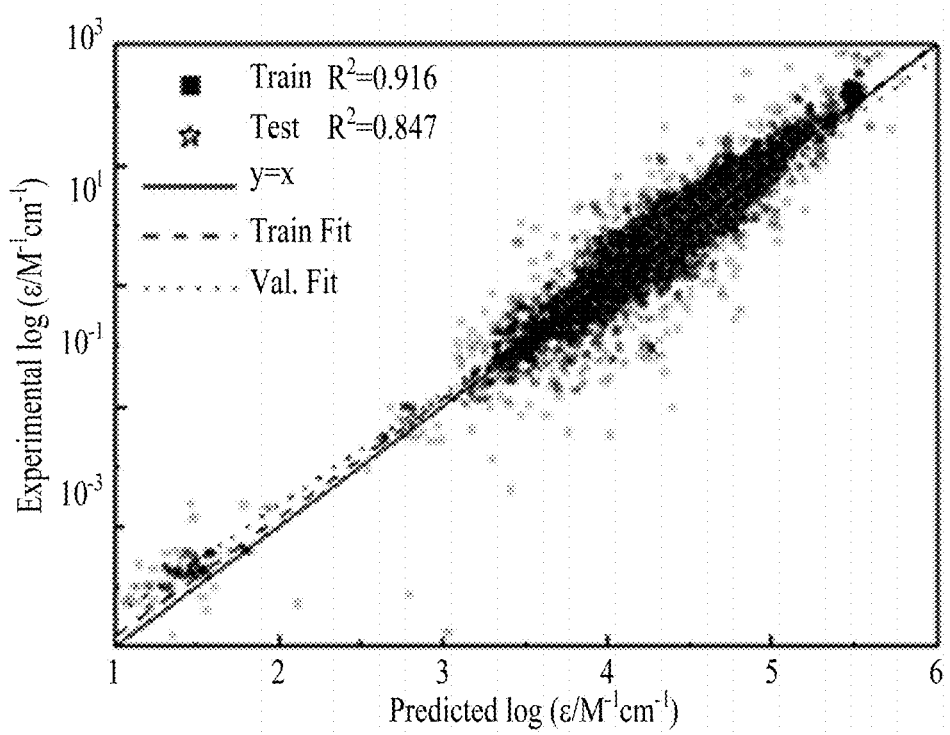

[FIG. 10]
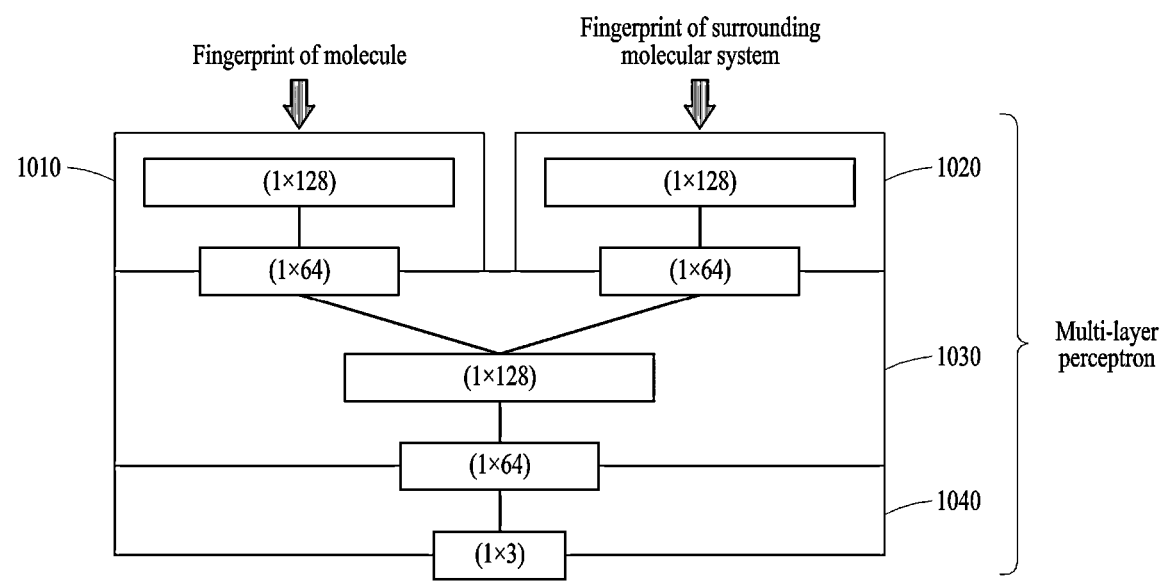

[FIG. 11A]
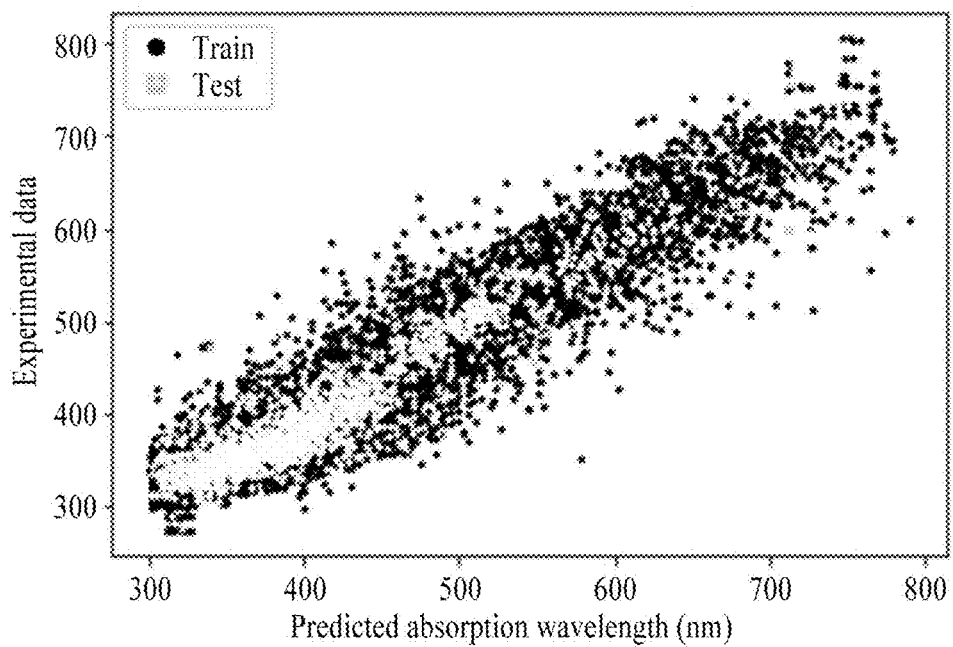

[FIG. 11B]
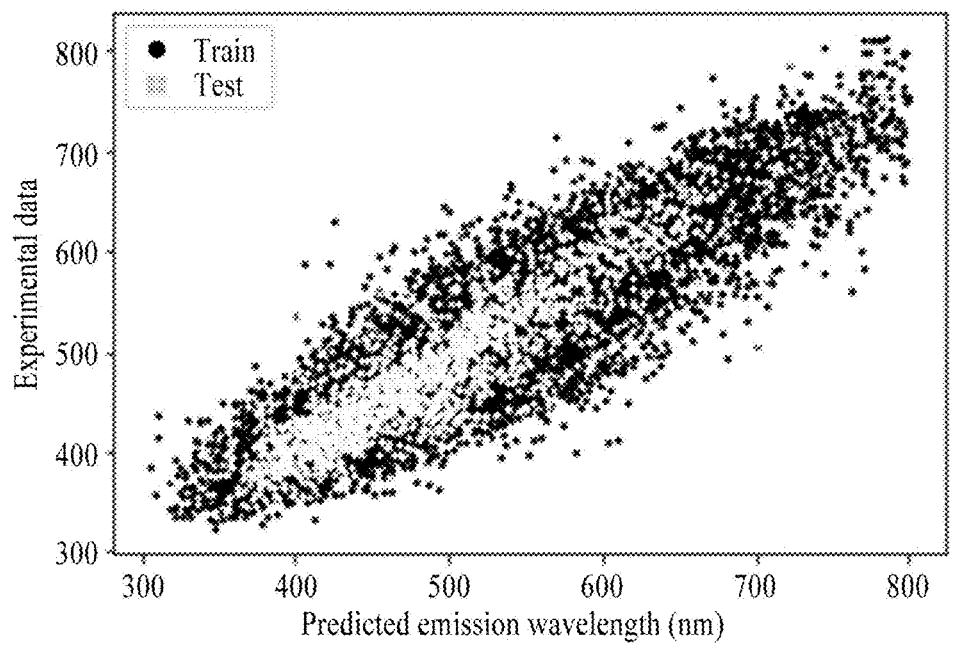

[FIG. 11C]
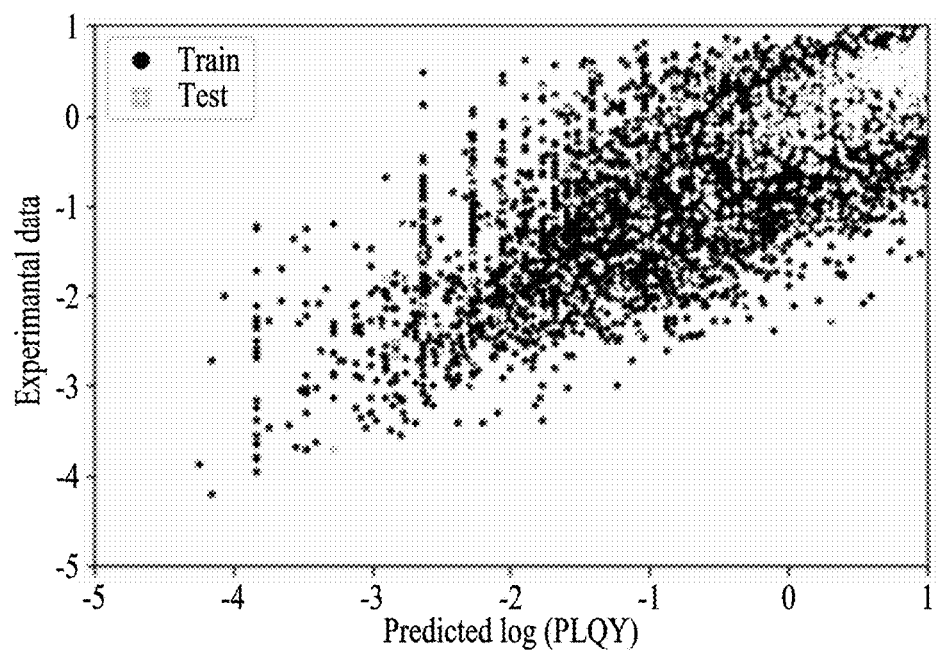

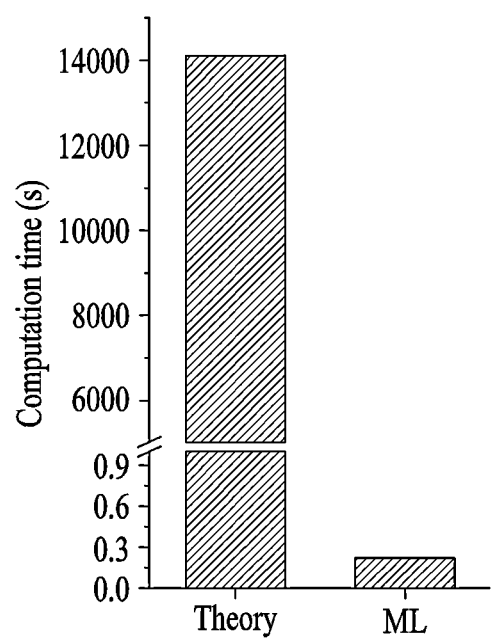
【FIG. 12A】

[FIG. 12B]
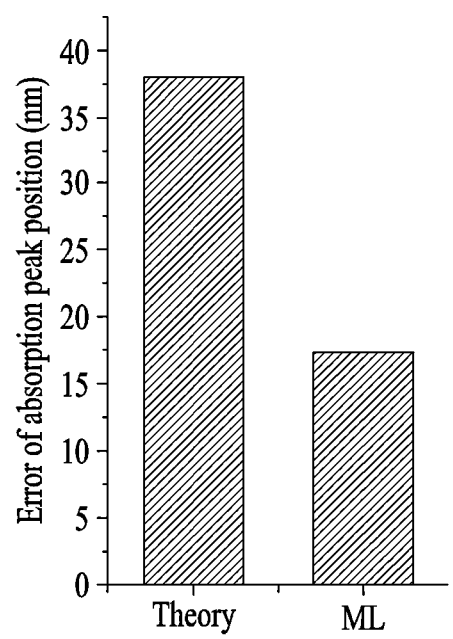

[FIG. 12C]
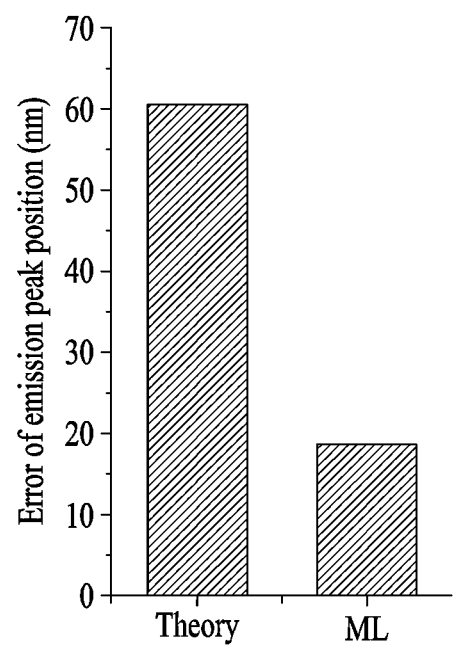

[FIG. 12D]
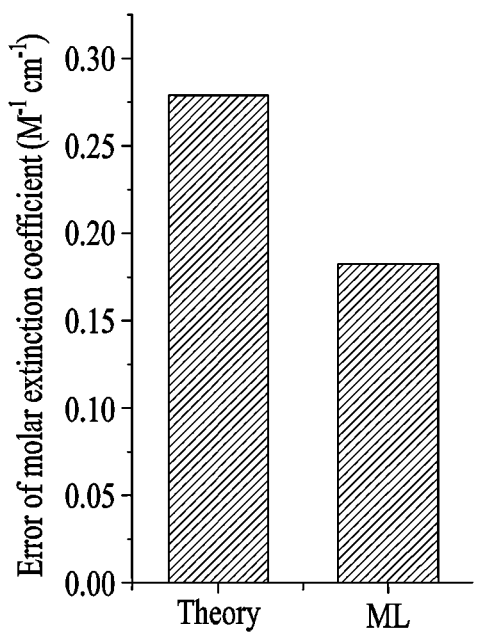

[FIG. 13A]
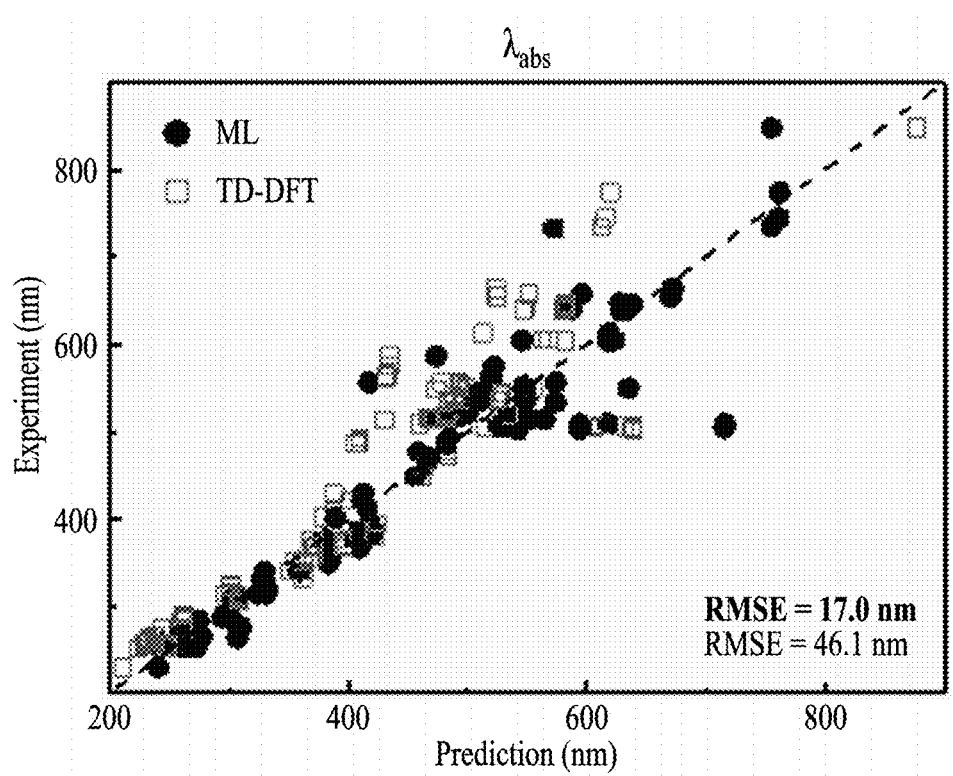

[FIG. 13B]
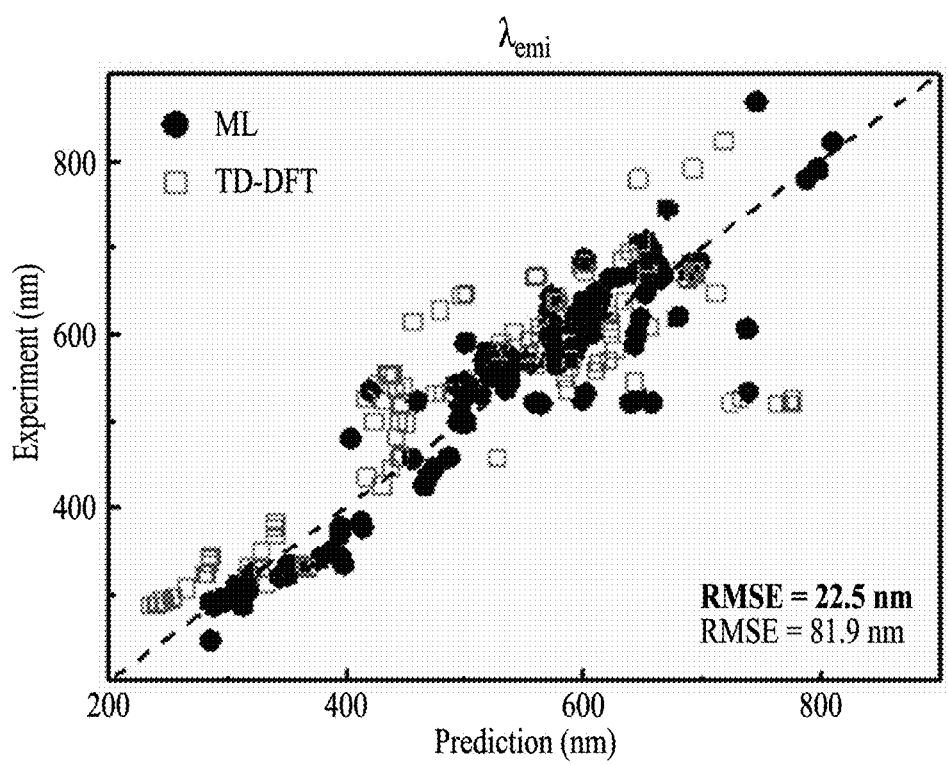

[FIG. 14A]
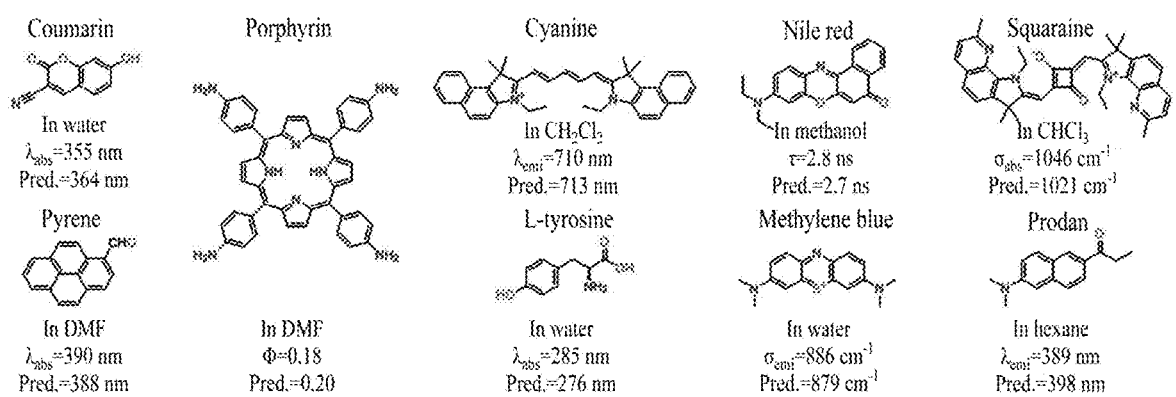

[FIG. 14B]
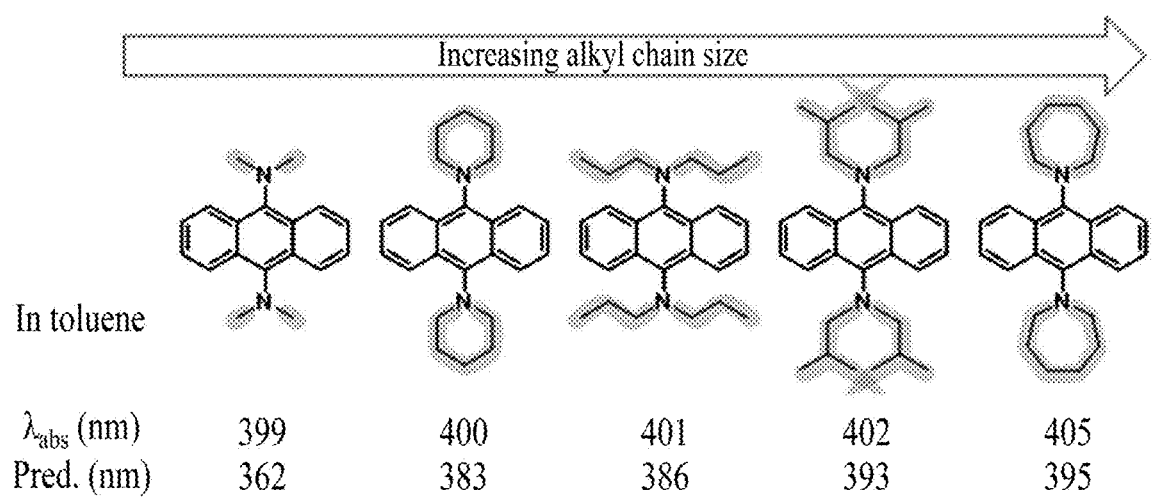

[FIG. 14C]
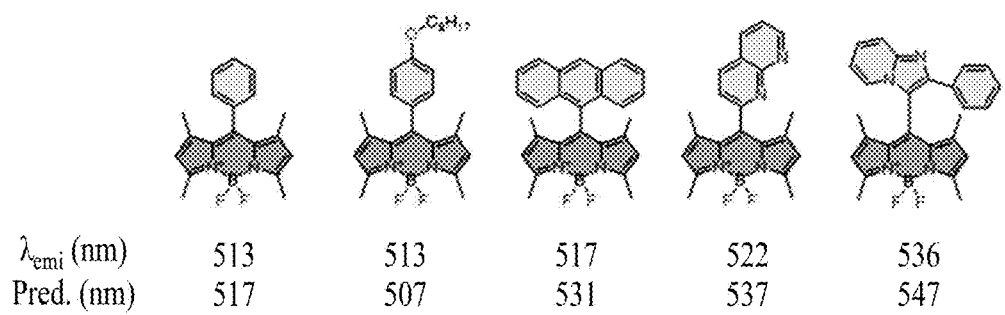

[FIG. 14D]
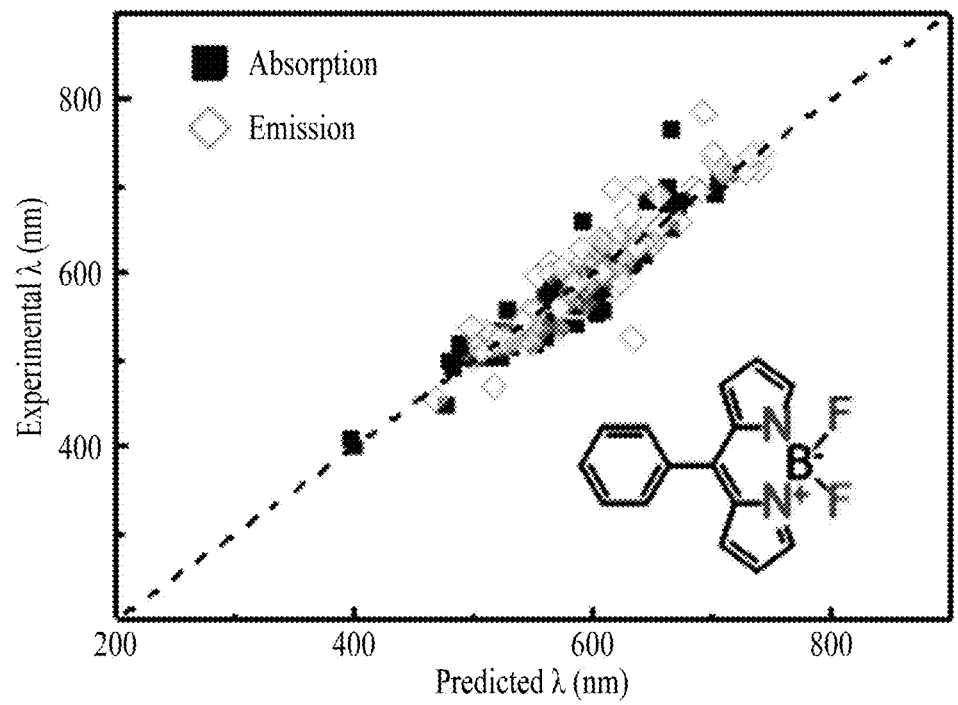
[FIG. 14E]
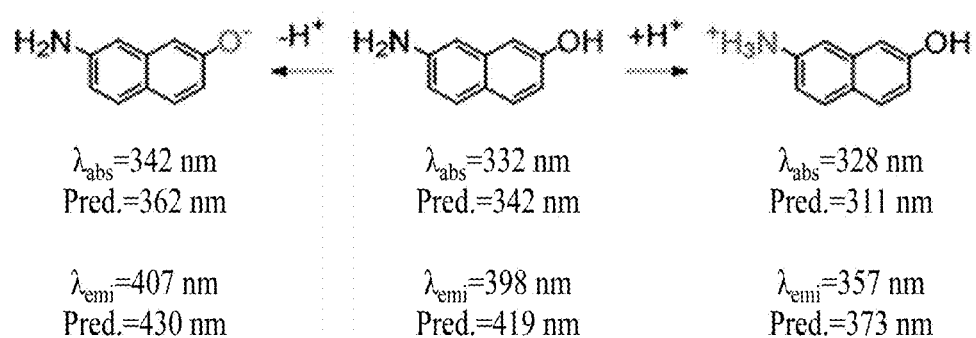

[FIG. 15A]
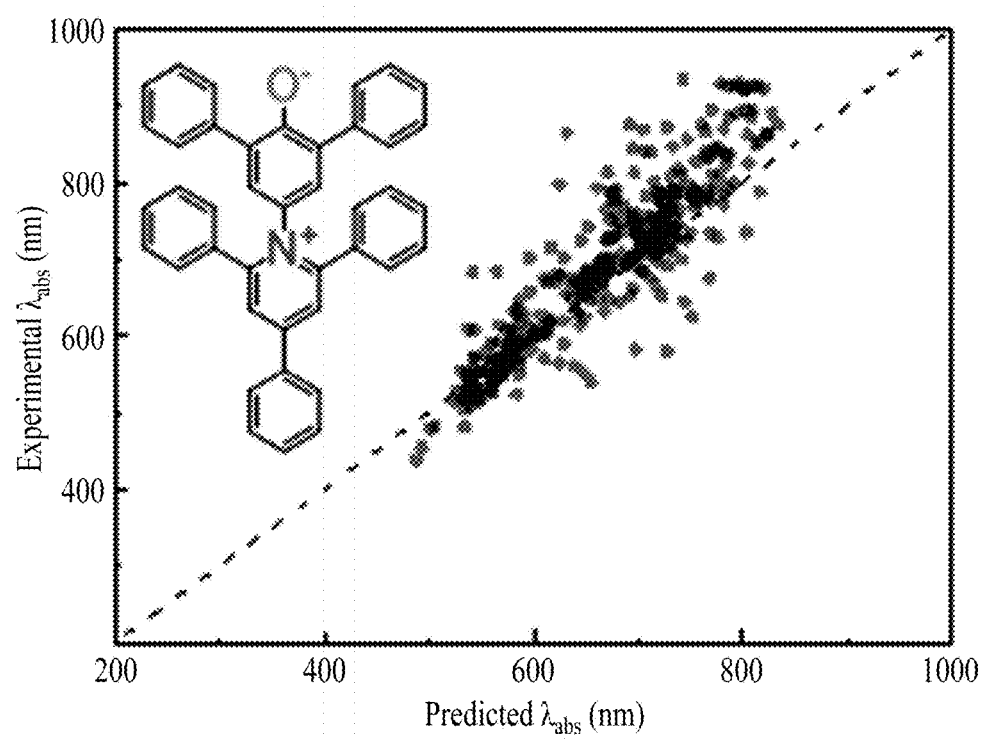

[FIG. 15B]
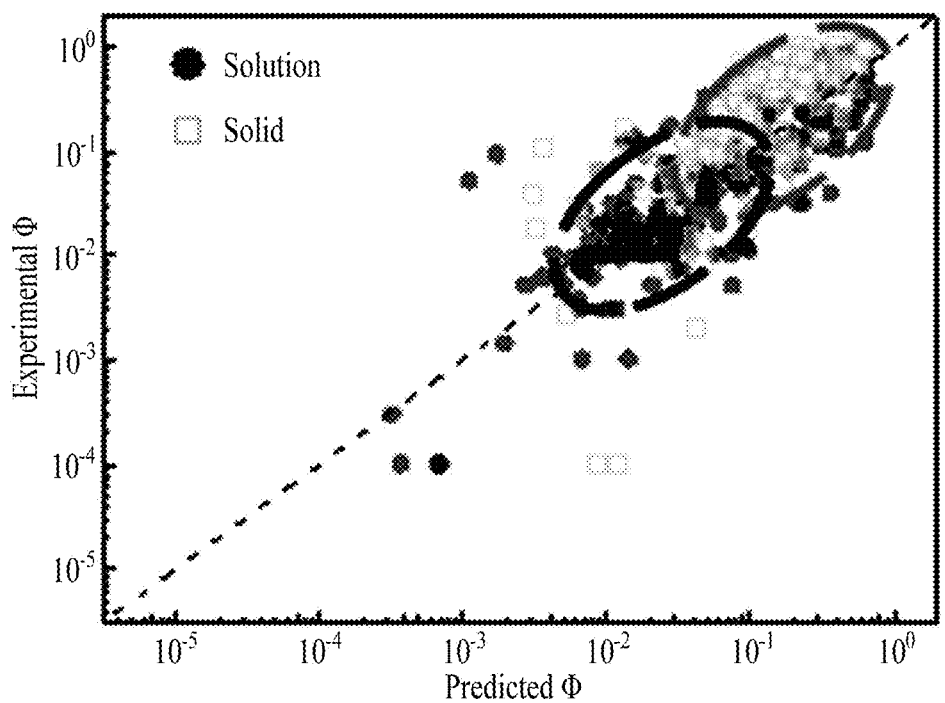

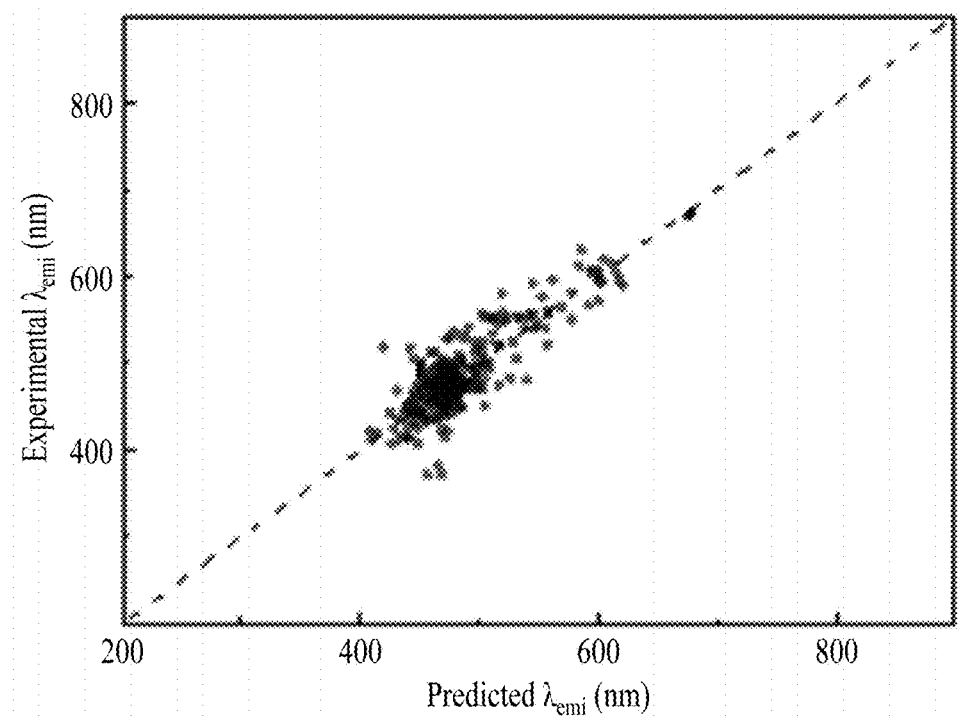
[FIG. 15C]

[FIG. 16]
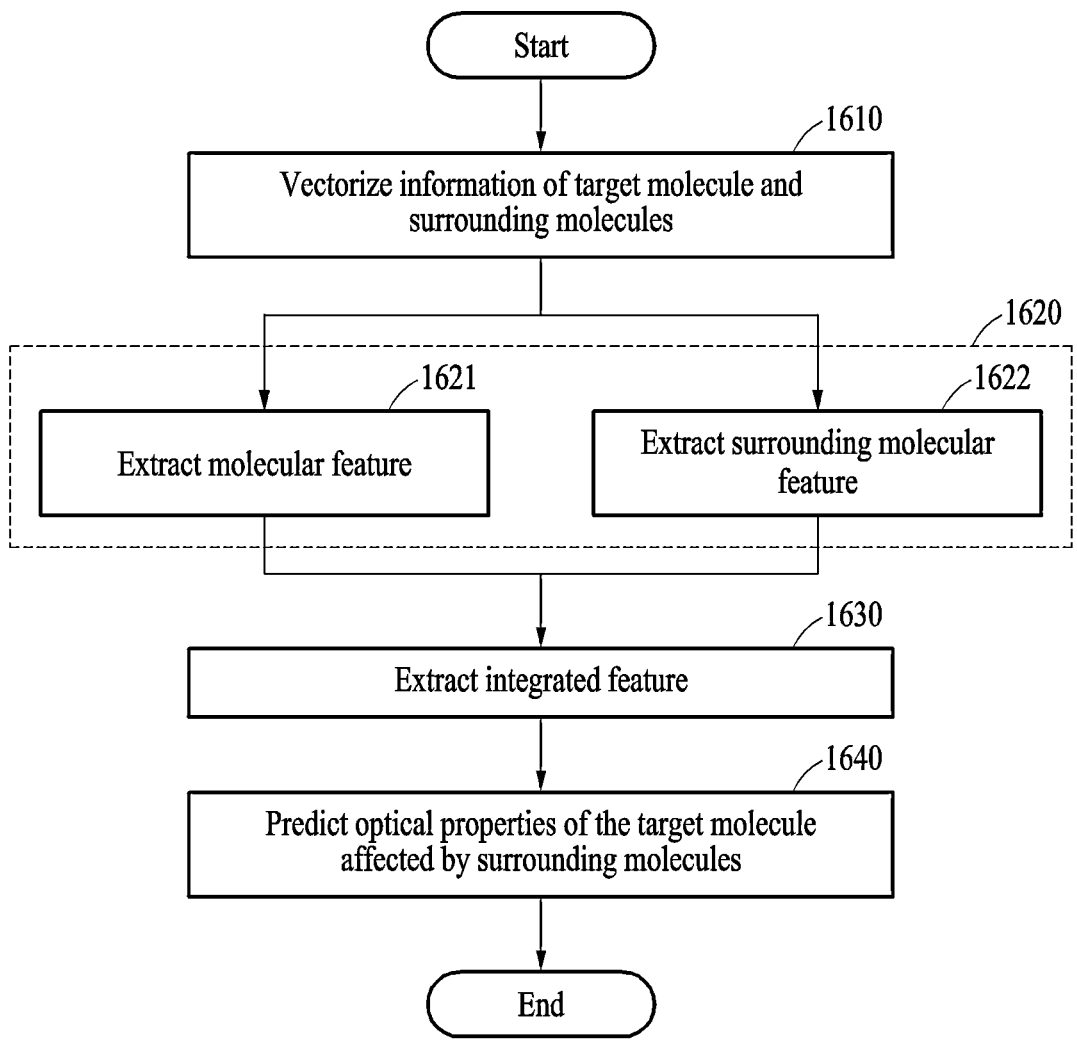

SYSTEM FOR PREDICTING OPTICAL PROPERTIES OF MOLECULES BASED ON MACHINE LEARNING AND METHOD THEREOF

CROSS-REFERENCE TO RELATED APPLICATION

This application claims the priority benefit of Korean Patent Application No. 10-2020-0031586, filed on Mar. 13, 2020, and Korean Patent Application No. 10-2020-0039313, filed on Mar. 31, 2020, in the Korean Intellectual Property Office, the disclosure of each of which is incorporated herein by reference.

BACKGROUND OF THE DISCLOSURE

Field of the Disclosure

The present disclosure relates to a system for predicting the optical properties of molecules based on machine learning and a method thereof, and more particularly, to a technical idea to predict the optical properties of a given target molecule using a machine learning method considering the interaction between the target molecule and surrounding molecules.

In addition, the present disclosure was derived from a study conducted as part of Core Research Institute of Science and Technology [Research foundation acknowledgement No. 2019R1A6A1A11044070, Research period: Mar. 1, 2020 to Feb. 28, 2021, Ministry name: Ministry of Education, Research management professional institution: National Research Foundation of Korea, Research project name: Core Research Institute of Science and Technology, Research project title: Research on π-electron-based energy-environmental innovation materials, Contribution rate: 10%, Host institution: Korea University Research and Business Foundation].

Description of the Related Art

Various optical properties, such as an absorption peak position and bandwidth, molar extinction coefficient, an emission peak position and bandwidth, emission lifetime, photoluminescence quantum yield, singlet and triplet energies, CIE 1931 color space, and a spin-orbit coupling constant, are key characteristics for developing various light-absorbing and luminescent materials such as organic light emitting diodes (OLEDs), dyes, fluorescent dyes, fluorescent sensors, and fluorescent markers for bioimaging.

In other words, a technology for quickly and accurately predicting the optical properties of molecules has attracted attentions in recent years. Such a technology is being widely used to develop light-absorbing and luminescent materials in various research fields.

Specifically, the color absorbed or emitted by the molecule can be easily estimated from the optical properties of the molecules. Such optical properties determine the performances of dyes, OLEDs, fluorescent markers for bioimaging, and the like.

Currently, the optimized structure, energy, absorption and fluorescence spectra, and infrared (IR) and Raman spectra of organic or inorganic molecules can be obtained using quantum chemical calculations.

In particular, the accuracy of a density functional theory (DFT) calculation is dependent on the DFT functionals and the basis sets.

Generally, DFT calculations require large computational costs and thus a high-performance computer is required. DFT calculations usually take several hours to several days depending on the molecular size.

In addition, using DFT calculations, it is impossible to practically estimate the photoluminescence quantum yield, emission lifetime, bandwidth, and the like among various optical properties of a molecule.

Therefore, there is a need for a new technology that can predict optical properties of molecules more rapidly and accurately than conventional methods and can predict optical properties that cannot be estimated using conventional methods.

RELATED ART DOCUMENT

Patent Document

Japanese Patent No. 5211347, "PROTEIN-COMPOUND INTERACTION PREDICTION METHOD"

SUMMARY OF THE DISCLOSURE

Therefore, the present disclosure has been made in view of the above problems, and it is an object of the present disclosure to provide an optical property prediction system and method which are capable of quickly and accurately predicting the optical properties of a target molecule, and thus, greatly reducing development time and cost.

It is another object of the present disclosure to provide the optical property prediction system and method based on machine learning using big-data which are capable of quickly and accurately predicting the optical properties of a given molecule affected by the surrounding molecules.

In accordance with an aspect of the present disclosure, the above objects can be accomplished by the provision of a system for predicting optical properties, including: a preprocessor that receives molecular information of a target molecule and surrounding molecules, and vectorizes the molecular information of a target molecule and surrounding molecules; a feature extractor that receives the vectorized information of the target molecule and surrounding molecules and extracts the features of the target molecule and surrounding molecules; an integrated feature extractor that receives both features of the target molecule and surrounding molecules and extracts the integrated feature of the target molecule and surrounding molecules by using an algorithm; and an optical property predictor that receives the integrated feature of the target molecule and surrounding molecules and predicts optical properties of the target molecule affected by surrounding molecules.

The feature extractor may further include: a molecular feature extractor that receives the vectorized information of the target molecule and extracts the feature of the target molecule by using an algorithm; and a surrounding molecular feature extractor that receives the vectorized information of surrounding molecules and extracts the feature of the surrounding molecules by using an algorithm.

The preprocessor may convert the molecular information of a target molecule and surrounding molecules into simplified molecular-input line-entry system (SMILES) expression and may vectorize the SMILES expressions of the target molecule and surrounding molecules.

The preprocessor may vectorize the SMILES expressions of the target molecule and surrounding molecules using at least one of molecular fingerprints, molecular descriptors, images of chemical structure, molecular graphs, molecular coordinates and one-hot encoded SMILES.

The molecular information of a target molecule and surrounding molecules may include the chemical structure.

The surrounding molecules may be solvent molecules in solution, host molecules in dopant-host systems, the same molecules in amorphous and crystalline solid states.

The surrounding molecules in gas phase may not be considered.

At least one of algorithms in the feature extractors and the integrated feature extractor may be a neural network algorithm including at least one hidden layer.

The optical properties may include at least one of the absorption peak position and bandwidth, molar extinction coefficient, emission peak position and bandwidth, emission lifetime, photoluminescence quantum yield, singlet and triplet energies, CIE 1931 color space, and spin-orbit coupling constants.

The present disclosure provides an optical property prediction method including: a preprocessor as the first step that receives molecular information of a target molecule and surrounding molecules, and vectorizes the molecular information of a target molecule and surrounding molecules; and a feature extractor as the second step that receives the vectorized information of the target molecule and surrounding molecules and extracts the features of the target molecule and surrounding molecules; and an integrated feature extractor as the third step receives both features of the target molecule and surrounding molecules and extracts the integrated feature of the target molecule and surrounding molecules; and an optical property predictor as the final step that receives the integrated feature of the target molecule and surrounding molecules and predicts optical properties of the target molecule affected by surrounding molecules.

The feature extractor may further include: a molecular feature extractor that receives the vectorized information of the target molecule and extracts the feature of the target molecule; a surrounding molecular feature extractor that receives the vectorized information of surrounding molecules and extracts the feature of the surrounding molecules.

In accordance with an embodiment, the present disclosure can quickly and accurately predict the optical properties of a target molecule, thereby being capable of greatly reducing development time and cost.

In accordance with an embodiment, the present disclosure based on machine learning can quickly and accurately predict the optical properties of a given molecule affected by the surrounding molecules.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 shows an optical property prediction system according to an embodiment;

FIG. 2 shows an example of implementing an optical property prediction system according to an embodiment;

FIG. 3 shows an operation process of an optical property prediction system according to an embodiment;

FIG. 4 shows an example of implementing a preprocessor according to an embodiment;

FIG. 5 shows an example of implementing a feature extractor according to an embodiment;

FIG. 6 shows an example of implementing an integrated feature extractor according to an embodiment;

FIG. 7 shows an example of implementing an optical property predictor according to an embodiment;

FIG. 8 shows a first operation example of an optical property prediction system according to an embodiment;

FIGS. 9A to 9E show the predicted optical properties according to the first operation example of the optical property prediction system according to an embodiment;

FIG. 10 shows a second operation example of an optical property prediction system according to an embodiment;

FIGS. 11A to 11C show the predicted optical properties according to the second operation example of the optical property prediction system according to an embodiment;

FIGS. 12A to 12D illustrate the performance comparison between the optical property prediction system and the conventional method;

FIGS. 13A to 13B illustrate the optical properties predicted by the optical property prediction system and the conventional method;

FIGS. 14A to 14E show various optical properties predicted by the optical property prediction system according to an embodiment;

FIGS. 15A to 15C show solvent effects on the optical properties predicted by the optical property prediction system according to an embodiment; and FIG. 16 shows an optical property prediction method according to an embodiment.

DETAILED DESCRIPTION OF THE DISCLOSURE

The present disclosure will now be described more fully with reference to the accompanying drawings, in which exemplary embodiments of the disclosure are shown.

This disclosure, however, should not be construed as limited to the exemplary embodiments and terms used in the exemplary embodiments, and should be understood as including various modifications, equivalents, and substituents of the exemplary embodiments.

Preferred embodiments of the present disclosure are now described more fully with reference to the accompanying drawings. In the description of embodiments of the present disclosure, certain detailed explanations of related known functions or constructions are omitted when it is deemed that they may unnecessarily obscure the essence of the disclosure.

In addition, the terms used in the specification are defined in consideration of functions used in the present disclosure, and can be changed according to the intent or conventionally used methods of clients, operators, and users. Accordingly, definitions of the terms should be understood on the basis of the entire description of the present specification.

In the drawings, like reference numerals in the drawings denote like elements.

As used herein, the singular forms "a," "an" and "the" are intended to include the plural forms as well, unless context clearly indicates otherwise.

Expressions such as "A or B" and "at least one of A and/or B" should be understood to include all possible combinations of listed items.

Expressions such as "a first," "the first," "a second" and "the second" may qualify corresponding components irrespective of order or importance and may be only used to distinguish one component from another component without being limited to the corresponding components.

In the case in which a (e.g., first) component is referred as "(functionally or communicatively) connected" or "attached" to another (e.g., second) component, the first component may be directly connected to the second component or may be connected to the second component via another component (e.g., third component).

In the specification, the expression " . . . configured to . . . (or set to)" may be used interchangeably, for example, with expressions, such as " . . . suitable for . . . ," " . . . having ability to . . . " " . . . modified to . . . ," " . . . manufactured to . . . ," " . . . enabling to . . . ," or " . . . designed to . . . ," in the case of hardware or software depending upon situations.

In any situation, the expression "a device configured to . . . " may refer to a device configured to operate "with another device or component."

For examples, the expression "a processor configured (or set) to execute A, B, and C" may refer to a specific processor performing a corresponding operation (e.g., embedded processor), or a general-purpose processor (e.g., CPU or application processor) executing one or more software programs stored in a memory device to perform corresponding operations.

In addition, the expression "or" means "inclusive or" rather than "exclusive or".

That is, unless otherwise mentioned or clearly inferred from context, the expression "x uses a or b" means any one of natural inclusive permutations.

In the aforementioned embodiments, constituents of the present disclosure were expressed in a singular or plural form depending upon embodiments thereof.

However, the singular or plural expressions should be understood to be suitably selected depending upon a suggested situation for convenience of description, and the aforementioned embodiments should be understood not to be limited to the disclosed singular or plural forms. In other words, it should be understood that plural constituents may be a singular constituent or a singular constituent may be plural constituents.

While the embodiments of the present disclosure have been described, those skilled in the art will appreciate that many modifications and changes can be made to the present disclosure without departing from the spirit and essential characteristics of the present disclosure.

Therefore, it should be understood that there is no intent to limit the disclosure to the embodiments disclosed, rather, the disclosure is to cover all modifications, equivalents, and alternatives falling within the spirit and scope of the disclosure as defined by the claims.

FIG. 1 shows an optical property prediction system according to an embodiment.

Referring to FIG. 1, an optical property prediction system 100 according to an embodiment may predict the optical properties of a target molecule affected by the surrounding molecules based on machine learning.

Specifically, conventional research to predict the optical properties of molecules use methods such as time-dependent Hartree-Fock (TD-HF) and time-dependent DFT (TD-DFT). However, methods such as TD-HF and TD-DFT require a very large computational cost. In addition, those methods are practically impossible to estimate the photoluminescence quantum yield, emission lifetime, bandwidth, and et cetera among various optical properties of a molecule.

On the other hand, the optical property prediction system 100 according to an embodiment is provided with a neural network-based model (machine learning model) constituted of at least one hidden layer; and receives molecular information of a target molecule and surrounding molecules as input to predict optical properties.

That is, since the optical property prediction system 100 does not require prior knowledge or intuition of an expert, subjective factors can be removed from the optical property prediction system 100 and the optical property prediction system 100 having higher generalization capability may be implemented. In addition, the optical property prediction system 100 may predict optical properties much faster (less than 1 second per molecule) and more accurately than a conventional method, and can even predict optical properties that cannot be estimated using conventional methods.

Hereinafter, the optical property prediction system 100 according to an embodiment will be described in more detail.

FIG. 2 shows an implementation example of an optical property prediction system according to an embodiment.

Referring to FIG. 2, an optical property prediction system 200 according to an embodiment can quickly and accurately predict the optical properties of a target molecule, thereby being capable of greatly reducing development time and cost.

In addition, the optical property prediction system 200 based on machine learning using big-data can quickly and accurately predict the optical properties of a target molecule affected by the surrounding molecules.

For this, the optical property prediction system 200 may include a preprocessor 210, a feature extractor 220, an integrated feature extractor 230 and an optical property predictor 240, and the feature extractor 220 may further include a molecular feature extractor 221 and a surrounding molecular feature extractor 222.

The preprocessor 210 according to an embodiment may receive molecular information of a target molecule and surrounding molecules, and vectorize the molecular information of a target molecule and surrounding molecules.

For example, the molecular information the molecular information of a target molecule and surrounding molecules may include the chemical structure. Here, the target molecule may be a chromophore or a luminescent molecule.

In addition, the molecular information of surrounding molecules may the surrounding molecules may be solvent molecules in solution, host molecules in dopant-host systems, the same molecules in amorphous and crystalline solid states. The surrounding molecules in gas phase may not be considered.

The preprocessor 210 may convert the molecular information of a target molecule and surrounding molecules into simplified molecular-input line-entry system (SMILES) expression and may vectorize the SMILES expressions of the target molecule and surrounding molecules. Here, SMILES refers to a specification in the form of a line notation for describing the structure of chemical species using short ASCII strings.

For example, the preprocessor 210 may vectorize the SMILES expressions of the target molecule and surrounding molecules using at least one of molecular fingerprints, molecular descriptors, images of chemical structure, molecular graphs, molecular coordinates and one-hot encoded SMILES which respectively correspond to the converted molecular information of target molecule and surrounding molecules. For example, the molecular coordinates may include three-dimensional coordinates (Cartesian coordinates) or Z-matrix of atoms in a molecule, but, without being limited thereto, may include all known molecular coordinates.

The feature extractor 220 according to an embodiment may receive the vectorized information of the target molecule and surrounding molecules and extract the features of the target molecule and surrounding molecules.

The molecular feature extractor 221 may receive the vectorized information of the target molecule and extract the feature of the target molecule by using an algorithm.

In addition, the surrounding molecular feature extractor 222 may receive the vectorized information of surrounding molecules and extract the feature of the surrounding molecules by using an algorithm.

The integrated feature extractor 230 according to an embodiment may receive both features of the target molecule and surrounding molecules and extract the integrated feature of the target molecule and surrounding molecules by using an algorithm.

At least one algorithm in the molecular feature extractor 221, in the surrounding molecular feature extractor 222, or in the integrated feature extractor 230 may be a neural network algorithm including at least one hidden layer.

At least one algorithm may be composed of an input layer, an output layer, and at least one hidden layer. Such a layer may be a neural network algorithm based on multilayer perceptron (MLP). In the algorithm, the input pass through the input layer, the hidden layers, and the output layer to predict properties. In the training process of the neural network, the weights and biases in the hidden layers may be optimized to reduce difference between the predicted and the true values.

An optical property predictor 240 according to an embodiment may receive the integrated feature of the target molecule and surrounding molecules and predict optical properties of the target molecule affected by surrounding molecules.

For example, the optical properties may include at least one of the absorption peak position and bandwidth, molar extinction coefficient, emission peak position and bandwidth, emission lifetime, photoluminescence quantum yield, singlet and triplet energies, CIE 1931 color space, and spin-orbit coupling constants.

In addition, the predicted properties of a target molecule may be verified by an expert or pre-stored big-data.

FIG. 3 is shows an operation process of an optical property prediction system according to an embodiment.

Referring to FIG. 3, an optical property prediction system 300 according to an embodiment may predict optical properties of a target molecule affected surrounding molecules using machine learning. For this, the optical property prediction system 300 may sequentially perform a SMILES conversion process, a vectorization process, a feature extraction process, an integrated feature extraction process and an optical property prediction process.

Specifically, in the SMILES conversion process, the molecular information of a target molecule (molecule) and surrounding molecules (surroundings) as inputs may be expressed as SMILES. That is, the SMILES conversion process may convert molecules into strings that can be recognized by a computer.

Next, the vectorization process may convert SMILESs of molecule and surroundings into vector formats which are appropriate for machine learning.

Next, in the feature extraction process, the features of molecule and surroundings may be extracted from the vector formats using the neural network algorithm.

Next, in the integrated feature extraction process, integrated feature may be extracted from the features of molecule and surroundings by using the neural network algorithm. That is, the integrated feature extraction process may give a result that contains the interactions between the molecule and surroundings.

Next, the optical property prediction process may predict the optical properties of the target molecule affected by surrounding molecules using the neural network algorithm.

FIG. 4 shows an example of implementing a preprocessor according to an embodiment.

Referring to FIG. 4, a preprocessor 400 according to an embodiment may receive molecular information of target molecule and surrounding molecules, may convert the molecular information into SMILES expression, and may vectorize SMILES expressions to the vectorized information (one-hot encoded SMILES).

The preprocessor 400 may vectorize the SMILES expressions of the target molecule and surrounding molecules using at least one of molecular fingerprints, molecular descriptors, images of chemical structure, molecular graphs, molecular coordinates and one-hot encoded SMILES. For example, the molecular coordinates may include three-dimensional coordinates (Cartesian coordinates) and Z-matrix of a molecule, but, without being limited thereto, may include all known molecular coordinates.

Specifically, the preprocessor 400 vectorize SMILES expressions of target molecule and surrounding molecules into the molecular fingerprint using at least one of fingerprint methods such as Molecular ACCess System (MACCS) key and Morgan fingerprints;
  into at least one of the molecular descriptors such as the number of rings, molecular weights, the number of hydrogen donors, logP and the number of rotatable bonds, but, without being limited thereto, all known molecular descriptors may be applied;
  into the images through a method of expressing an RGB value for each position of the images or a method of expressing using a value in a grey-scale;
  into an edge matrix representing how molecules are connected and a node matrix representing information of atoms in molecules; or
  into Z-matrix expressed as internal coordinates such as bond lengths, bond angles, and dihedral angles of atoms in a molecule or three-dimensional coordinates (Cartesian coordinates) of atoms in a molecule.

FIG. 5 shows an example of implementing a feature extractor according to an embodiment.

Referring to FIG. 5, the feature extractor 500 according to an embodiment may receive the vectorized information of the target molecule and surrounding molecules and extract the features of the target molecule and surrounding molecules.

In other words, the features of the target molecule and surrounding molecules may be used as input of an integrated feature extractor.

The feature extractor 500 may be composed of a molecular feature extractor and a surrounding molecular feature extractor, which may respectively receive the vectorized information of the target molecule and surrounding molecules and respectively extract the features of the target molecule and surrounding molecules.

The algorithms in the molecular feature extractor and the surrounding molecular feature extractor may be composed of only a MLP.

The algorithms in the molecular feature extractor and the surrounding molecular feature extractor may contain additional machine learning methods other than a MLP such as convolutional neural network (CNN) for an image, recurrent neural network (RNN) for an one-hot encoded string, and graph convolutional network (GCN) for a graph.

FIG. 6 shows an example of implementing an integrated feature extractor according to an embodiment.

Referring to FIG. 6, an integrated feature extractor 600 according to an embodiment may receive both features of the target molecule and surrounding molecules and extract the integrated features of the target molecule and surrounding molecules by using an algorithm. An algorithm in the integrated feature extractor 600 may be composed of a MLP.

FIG. 7 shows an example of implementing an optical property predictor according to an embodiment.

Referring to FIG. 7, an optical property predictor 700 according to an embodiment may receive the integrated features of the target molecule and surrounding molecules and predict optical properties of the target molecule affected by surrounding molecules. The algorithms in the optical property may be composed of a MLP.

Here, the optical property predictor 700 may predict one optical property of the absorption peak position and bandwidth, molar extinction coefficient, emission peak position and bandwidth, emission lifetime, photoluminescence quantum yield, singlet and triplet energies, CIE 1931 color space, and spin-orbit coupling constants or may simultaneously predict at least two optical properties thereof.

FIG. 8 shows a first operation example of an optical property prediction system according to an embodiment.

Referring to FIG. 8, in an optical property prediction system 800 according to an embodiment, a molecule feature extractor 810 and a surrounding molecular feature extractor 820 may respectively receive the vectorized information of the target molecule and surrounding molecules in a form of molecular graphs and may respectively extract the features of the target molecule and surrounding molecules.

For example, algorithms in the molecule feature extractor 810 and the surrounding molecular feature extractor 820 may be respectively composed of 6-layer GCN for graph convolution of edge and node matrices, and 1-layer MLP consisting of 512 elements.

The extracted features of target molecule and surrounding molecules may be concatenated in an integrated feature extractor 830 and may pass through 1-layer MLP consisting of 512 elements, so that the integrated feature may be extracted. The extracted integrated feature may be an input of an optical property predictor 840 so that the optical properties may be predicted.

The optical property predictor 840 may predict properties of the absorption peak position, molar extinction coefficient, an emission peak position, emission lifetime, photoluminescence quantum yield.

FIGS. 9A to 9E show the predicted optical properties according to the first operation example of the optical property prediction system according to an embodiment.

Referring to FIGS. 9A to 9E, FIGS. 9A to 9E show the plots of predicted versus actual measurement results after simultaneously training the absorption peak position ($\lambda_{abs}$), emission peak position ($\lambda_{flu}$), emission lifetime (t), photoluminescence quantum yield ($\Phi$), and molar extinction coefficient (log$\varepsilon$) of 30,094 molecules collected from the literatures. The square of the Pearson correlation coefficient ($R^2$) is calculated to show accuracies of prediction.

From FIGS. 9A to 9E, it can be confirmed that the optical property prediction system according to an embodiment is well trained to more accurately predict the target molecules in surrounding molecules.

FIG. 10 shows a second operation example of an optical property prediction system according to an embodiment.

Referring to FIG. 10, in an optical property prediction system 1000 according to an embodiment, a molecule feature extractor 1010 and a surrounding molecular feature extractor 1020 may respectively receive the vectorized information of the target molecule and surrounding molecules in a form of molecular fingerprint and may respectively extract the features of the target molecule and surrounding molecules.

For example, algorithms in the molecule feature extractor 1010 and the surrounding molecular feature extractor 1020 may be respectively composed of 1-layer MLP consisting of 64 elements.

The extracted features of target molecule and surrounding molecules may be concatenated in an integrated feature extractor 1030 and may pass through 1-layer MLP consisting of 64 elements, so that integrated feature may be extracted. The extracted integrated feature may be an input of an optical property predictor 1040.

The optical property predictor 1040 may predict properties of the absorption peak position, emission peak position, photoluminescence quantum yield.

FIGS. 11A to 11C show the predicted optical properties according to the second operation example of the optical property prediction system according to an embodiment.

Referring to FIGS. 11A to 11C, FIGS. 11A to 11C show the plots of predicted versus actual measurement results after simultaneously training the absorption peak position, emission peak position, photoluminescence quantum yield of 30,094 molecules collected from the literatures.

As shown in FIGS. 11A to 11C, it can be confirmed that the optical property prediction system based on fingerprints according to an embodiment is successfully predict the target molecules affected by surrounding molecules as in the first operation example based on molecular graphs described with reference to FIG. 8.

FIGS. 12A to 12D illustrate the performance comparison between the optical property prediction system and the conventional method.

Referring to FIGS. 12A to 12D, FIGS. 12A to 12D show computation times per molecule, errors in predicted absorption peak positions, errors in predicted emission peak positions and errors in predicted molar extinction coefficients using the optical property prediction system (ML) according to an embodiment and a known conventional method, TD-DFT (Theory).

As shown in FIGS. 12A to 12D, the ML according to an embodiment, can reduce a computation time per molecule by 63,000 times, the error of the absorption peak position by 2.2 times, the error of the emission peak position by 3.2 times, and the error of the molar extinction coefficient by 1.5 times, compared to the Theory.

That is, the ML according to an embodiment can shorten a calculation cost and improve an accuracy of prediction, compared to the Theory.

FIGS. 13A to 13B illustrate the performance comparison between the optical property prediction system and the conventional method.

Referring to FIGS. 13A to 13B, FIGS. 13A to 13B show the plots of the absorption peak position ($\lambda_{abs}$) and emission peak position ($\lambda_{emi}$) predicted by the optical property prediction system (ML) according to an embodiment and a known conventional method (TD-DFT). In addition, the root-mean-squared-errors (RMSEs) are calculated to show accuracies of prediction of two methods. It was confirmed that RMSE of predicted properties by the optical property prediction system (ML) is 2 to 3 times smaller than a predicted value of the existing technology (TD-DFT). Specifically, the RMSEs of predicted $\lambda_{abs}$ and $\lambda_{emi}$ by the optical property prediction system (ML) are calculated to be 17.0 nm and 22.5 nm, respectively.

FIGS. 14A to 14E show various optical properties predicted by the optical property prediction system according to an embodiment.

Referring to FIGS. 14A to 14E, FIG. 14A illustrates various optical properties of chromophores with different molecular structures (coumarin, porphyrin, cyanine, nile red, squaraine, pyrene, L-tyrosine, methylene blue, prodan), which are obtained using the optical property prediction system according to an embodiment, FIG. 14B illustrates the absorption peak position ($\lambda_{abs}$) of N,N-dialkylamine-modified anthracene derivatives with various alkyl chain lengths, and FIG. 14C illustrates the emission peak position ($\lambda_{emi}$) values of BODIPY derivatives with different moieties at the meso position.

In addition, FIG. 14D illustrates Experimental vs. predicted absorption and emission peak position ($\lambda_{emi}$) of 97 molecules structurally similar to BODIPY derivatives, and FIG. 14E illustrates the protonation states of 7-amino-2-naphthol in water and their experimentally measured and predicted the absorption peak position ($\lambda_{abs}$) and emission peak position ($\lambda_{emi}$).

As shown in FIGS. 14A to 14E, the optical properties of the organic compound modified with various functional groups can be easily predicted by the optical property prediction system according to an embodiment.

For example, as shown in FIG. 14B, various N,N-dialkylamine-modified anthracene derivatives of which the absorption peak position ($\lambda_{abs}$) values have been experimentally determined and the optical property prediction system may successfully predict the absorption peak position ($\lambda_{abs}$) of these derivatives. The predicted the absorption peak position ($\lambda_{abs}$) get red-shifted with increasing the alkyl chain length because the optical property prediction system recognises the electron-donating ability of the alkyl chain.

The core moieties with the greatest effect on the overall optical properties of the molecules are recognised by the optical property prediction system. Specifically, the molecules shown in FIG. 14C include 4,4-difluoro-4-bora-3a, 4diaza-s-indacene (BODIPY) as a core part, and the optical property prediction system can recognize that the BODIPY moiety affected the emission peak position ($\lambda_{emi}$) more than the other moieties.

For the anthracene (donor)-BODIPY (acceptor) structure, the emission peak position ($\lambda_{emi}$) of BODIPY is longer than that of anthracene, and thus, BODIPY determines the emission peak position ($\lambda_{emi}$) of the molecule according to Kasha's rule.

As shown in FIG. 14D, it can be confirmed that the optical property prediction system according to an embodiment can easily distinguish and predict the optical properties of chromophores having similar structures. Specifically, the optical property prediction system can recognize different core structures and direct modifications to core structures that lead to significant changes in the optical properties, i.e., changes in the conjugation length and substituents of the core structures. The predicted and experimental $\lambda_{abs}$ and $\lambda_{emi}$ values of 97 chromophores are presented in FIG. 14D. The diverse changes in the core structures were successfully accounted for in the prediction of the optical properties.

Meanwhile, the optical property prediction system according to an embodiment may accurately identify protonation and deprotonation that are important in acid-base equilibrium and acid catalysis as shown in FIG. 14E. Specifically, The protonated and deprotonated forms are distinguished in the optical property prediction system by the feature matrix in terms of the number of hydrogen atoms and formal charge at the protonation site.

FIGS. 15A to 15C show solvent effects on the optical properties predicted by the optical property prediction system according to an embodiment.

Referring to FIGS. 15A to 15C, FIG. 15A illustrates experimental versus predicted absorption peak positions ($\lambda_{abs}$) of Reichardt's dye (Betaine 30) in 334 solvents, FIG. 15B depicts experimental versus predicted photoluminescence quantum yields ($\Phi$) of molecules exhibiting aggregation induced emission in solution or in the solid phase, and FIG. 15C illustrates experimental versus predicted emission peak positions ($\lambda_{emi}$) of dopants in host matrices (films).

From FIGS. 15A to 15C, it can be confirmed that the optical property prediction system according to an embodiment can accurately predict solvent effects on the absorption and emission spectra. In the optical property prediction system, interactions between the target molecule and surrounding molecules are included, allowing accurate prediction of solvatochromic shifts.

As shown in FIG. 15A, it can be confirmed that the absorption peak position ($\lambda_{abs}$) of the Reichardt's dye (Betaine 30) is exhibits a hypsochromic (blue) shift from 1000 to 450 nm with increasing solvent polarity. In addition, the solvatochromic shifts of 334 solvent molecules over 500 nm are well predicted by the optical property prediction system.

In the IEF-PCM model, solvation is treated in a simple manner, and the solvent effect is directly associated with the dielectric constant. Therefore, the effects of solvent molecules with similar dielectric constants are poorly distinguished. However, the optical property prediction system accurately predicted the absorption wavelengths of Betaine 30 in solvents with similar dielectric constants.

In addition, it can be confirmed that the prediction model of the optical property prediction system according to an embodiment can accurately predict the photoluminescence quantum yield ($\Phi$) of a given molecule in various states such as a solution state or a solid state, and the matrix effect on the emission properties of dopants as well, as shown in FIGS. 15B and 15C.

FIG. 16 shows an optical property prediction method according to an embodiment.

In other words, FIG. 16 illustrates a method of operating the optical property prediction system according to an embodiment described with reference to FIGS. 1 to 15, and descriptions, overlapping with those described with reference to FIGS. 1 to 15, among contents described through FIG. 16 below are omitted.

Referring to FIG. 16, in step 1610 of an optical property prediction method according to an embodiment, a preprocessor may receive molecular information of a target molecule and surrounding molecules, and vectorizes the molecular information of a target molecule and surrounding molecules.

Next, in step 1620 of the optical property prediction method according to an embodiment, a feature extractor may receive the vectorized information of the target molecule and surrounding molecules and extract the features of the target molecule and surrounding molecules.

In step 1621 of the optical property prediction method according to an embodiment, a molecular feature extractor may receive the vectorized information of the target molecule and extract the features of the target molecule by using an algorithm.

In addition, in step 1622 of the optical property prediction method according to an embodiment, a surrounding molecular feature extractor may receive the vectorized information of surrounding molecules and extract the features of the surrounding molecules by using an algorithm.

Next, in step 1630 of the optical property prediction method according to an embodiment, an integrated feature extractor may receive both features of the target molecule and surrounding molecules and extract the integrated features of the target molecule and surrounding molecules by using an algorithm.

Next, in step 1640 of the optical property prediction method according to an embodiment, an optical property predictor may receive the integrated features of the target molecule and surrounding molecules and predict optical properties of the target molecule affected by surrounding molecules.

In conclusion, the present disclosure can quickly and accurately predict the optical properties of a target molecule, thereby being capable of greatly reducing development time and cost.

In addition, the present disclosure based on machine learning using big-data can quickly and accurately predict the optical properties of a given molecule affected by the surrounding molecules.

Although the present disclosure has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

DESCRIPTION OF SYMBOLS

200: optical property prediction system 210: preprocessor
220: feature extractor 221: molecular feature extractor
222: surrounding molecular feature extractor 230: integrated feature extractor
240: optical property predictor

What is claimed is:

1. A system for predicting optical properties, the system comprising:
   at least one processor configured to perform an operation of a preprocessor, a feature extractor, a molecular feature extractor, a surrounding molecular feature extractor, an integrated feature extractor, and an optical property predictor,
   wherein the preprocessor receives molecular information of a target molecule and surrounding molecules and vectorizes the molecular information of the target molecule and the surrounding molecules;
   wherein the feature extractor receives the vectorized information of the target molecule and the surrounding molecules and extracts features of the target molecule and the surrounding molecules through a parallel feature extraction process utilizing independent neural network algorithms, wherein the feature extractor comprises:
   wherein the molecular feature extractor receives the vectorized information of the target molecule and extracts the features of the target molecule utilizing a first algorithm, and
   wherein the surrounding molecular feature extractor receives the vectorized information of the surrounding molecules and extracts the features of the surrounding molecules utilizing a second algorithm;
   wherein the integrated feature extractor receives both the features of the target molecule and the surrounding molecules and extracts integrated features of the target molecule and the surrounding molecules through an integrated feature extraction process utilizing a third algorithm;
   wherein the optical property predictor receives the integrated features of the target molecule and the surrounding molecules and predicts optical properties of the target molecule affected by the surrounding molecules;
   wherein the molecular information of the target molecule and the surrounding molecules includes a chemical structure;
   wherein the target molecule is a chromophore or a luminescent molecule; and
   wherein the molecular information of the surrounding molecules includes at least one of solvent molecules in a solution, host molecules in dopant-host systems, and the same molecules in amorphous and crystalline solid states.

2. The system according to claim 1, wherein the preprocessor converts the molecular information of the target molecule and the surrounding molecules into simplified molecular-input line-entry system (SMILES) expression and vectorizes the converted molecular information of the target molecule and the surrounding molecules.

3. The system according to claim 2, wherein the preprocessor vectorize the SMILES expressions of the target molecule and the surrounding molecules using at least one of molecular fingerprints, molecular descriptors, images of the chemical structure, molecular graphs, molecular coordinates, and one-hot encoded SMILES.

4. The system according to claim 1, wherein at least one of algorithms in the feature extractor and the integrated feature extractor is a neural network algorithm including at least one hidden layer.

5. The system according to claim 1, wherein the optical properties include at least one of absorption peak position and bandwidth, molar extinction coefficient, emission peak position and bandwidth, emission lifetime, photoluminescence quantum yield, singlet and triplet energies, CIE 1931 color space, and spin-orbit coupling constants.

6. A processor-implemented optical property prediction method,
   the method including:
   receiving, by a preprocessor, molecular information of a target molecule and surrounding molecules, and vectorizing the molecular information of the target molecule and the surrounding molecules;
   receiving, by a feature extractor, the vectorized information of the target molecule and the surrounding molecules and extracting features of the target molecule and the surrounding molecules through a parallel feature extraction process utilizing independent neural network algorithms, wherein the feature extractor comprises:
   a molecular feature extractor receives the vectorized information of the target molecule and extracts the features of the target molecule utilizing a first algorithm, and
   a surrounding molecular feature extractor receives the vectorized information of the surrounding molecules and extracts the features of the surrounding molecules utilizing a second algorithm;

receiving, by an integrated feature extractor, both the features of the target molecule and the surrounding molecules and extracting integrated features of the target molecule and the surrounding molecules through an integrated feature extraction process utilizing a third algorithm; and receiving, by an optical property predictor, the integrated features of the target molecule and the surrounding molecules and predicting optical properties of the target molecule affected by the surrounding molecules, wherein the molecular information of the target molecule and the surrounding molecules includes a chemical structure;

wherein the target molecule is a chromophore or a luminescent molecule; and wherein the molecular information of the surrounding molecules includes at least one of solvent molecules in a solution, host molecules in dopant-host systems, and the same molecules in amorphous and crystalline solid states.

* * * * *